US007879992B2

(12) United States Patent
Vickers et al.

(10) Patent No.: US 7,879,992 B2
(45) Date of Patent: Feb. 1, 2011

(54) MODIFICATION OF MYD88 SPLICING USING MODIFIED OLIGONUCLEOTIDES

(75) Inventors: Timothy Vickers, Oceanside, CA (US); Nicholas M. Dean, Olivenhain, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 284 days.

(21) Appl. No.: 11/339,785

(22) Filed: Jan. 24, 2006

(65) Prior Publication Data
US 2006/0172962 A1     Aug. 3, 2006

Related U.S. Application Data

(60) Provisional application No. 60/648,823, filed on Jan. 31, 2005.

(51) Int. Cl.
*C07H 21/04* (2006.01)
(52) U.S. Cl. .................................... 536/24.5
(58) Field of Classification Search ................ 536/24.5
See application file for complete search history.

(56) References Cited

U.S. PATENT DOCUMENTS

| | | | |
|---|---|---|---|
| 5,627,274 A | 5/1997 | Kole et al. | |
| 5,665,593 A | 9/1997 | Kole et al. | |
| 5,801,154 A | 9/1998 | Baracchini et al. | |
| 5,916,808 A | 6/1999 | Kole et al. | |
| 5,976,879 A | 11/1999 | Kole et al. | |
| 6,183,966 B1 * | 2/2001 | Gray et al. | 435/6 |
| 6,210,892 B1 | 4/2001 | Bennett et al. | |
| 7,033,830 B2 * | 4/2006 | Karras et al. | 435/375 |
| 2002/0049173 A1 | 4/2002 | Bennett et al. | |
| 2003/0186903 A1 | 10/2003 | Karras et al. | |
| 2003/0228597 A1 | 12/2003 | Cowsert et al. | |
| 2004/0038926 A1 | 2/2004 | Karras et al. | |
| 2005/0059071 A1 | 3/2005 | Eriksson et al. | |
| 2005/0181476 A1 | 8/2005 | Beyaert et al. | |
| 2006/0211642 A1 * | 9/2006 | McSwiggen et al. | 514/44 |
| 2007/0031844 A1 * | 2/2007 | Khvorova et al. | 435/6 |
| 2007/0031850 A1 * | 2/2007 | Mounts et al. | 435/6 |

FOREIGN PATENT DOCUMENTS

| | | |
|---|---|---|
| WO | WO 94/26887 A1 | 11/1994 |
| WO | WO 02/38738 A2 | 5/2002 |
| WO | WO 03046132   * | 6/2003 |

OTHER PUBLICATIONS

Tuschl et al. (The siRNA user guide, 2001).*
Adachi, O. et al., "Targeted Disruption of the *MyD88* Gene Results in Loss of IL-I- and IL-18-Mediated Function," *Immunity* (1998) 9:143-150.
Björkbacka, H. et al., "Reduced atherosclerosis in MyD88-null mice links elevated serum cholesterol levels to activation of innate immunity signaling pathways," *Nature Med.* (2004) 10(4):416-421.
Burns, K. et al., "MyD88, an Adapter Protein Involved in Interleukin-1 Signaling,"*J. Biol. Chem.* (1998) 273(20):12203-12209.
Burns, K. et al., "Inhibition of Interleukin I Receptor/Toll-like Receptor Signaling through the Alternatively Spliced, Short Form of MyD88 Is Due to Its Failure to Recruit IRAK-4,"*J. Exp. Med.* (2003) 197(2):263-268.
Cao, Z. et al., "TRAF6 is a signal transducer for interleukin-1", *Nature* (1996) 383:443-444.
Cartegni, L. et al., "Correction of disease-associated exon skipping by synthetic exon-specific activators," *Nature Structural Biol.* (2003) 10(2):120-125.
Garcia-Blanco, M. A. et al., "Alternative splicing in disease and therapy," *Nature Biotech.* (2004) 22(5):535-546.
Harborth, J. et al., "Sequence, Chemical, and Structural Variation of Small Interfering RNAs and Short Hairpin RNAs and the Effect on Mammalian Gene Silencing," *Antisense Nucl. Acid Drug Dev.* (2003) 13:83-105.
Hardiman, G. et al., "Genetic Structure and Chromosomal Mapping of MyD88," *Genomics* (1997) 45:332-339.
Jenssens, S. et al., "Regulation of Interleukin-1—and Lipopolysaccharide-Induced NF-κB Activation by Alternative Splicing of MyD88," *Curr. Biol.* (2002) 12:467-471.
Karras, J. G. et al., "Deletion of Individual Exons and Induction of Soluble Murine Interleukin-5 Receptor-α Chain Expression through Antisense Oligonucleotide-Mediated Redirection of Pre-mRNA Splicing," *Mol. Pharmacol.* (2000) 58:380-387.
Kawai, T. et al., "Unresponsiveness of MyD88-Deficient Mice to Endotoxin," *Immunity* (1999) 11:115-122.
Medzhitov, R. et al., "MyD88 Is an Adaptor Protein in the hToll/IL-1 Receptor Family Signaling Pathways," *Mol. Cell* (1998) 2:253-258.
Sazani, P. et al., "Therapeutic potential of antisense oligonucleotides as modulators of alternative splicing," *J. Clin. Invest.* (2003) 112(4):481-486.
Scaffidi, P. et al., "Reversal of the cellular phenotype in the premature aging disease Hutchinson-Gilford progeria syndrome," *Nature Med.* (2005) 11(4):440-445.
Taylor, J. K. et al., "Induction of endogenous Bcl-xS through the control of Bcl-x pre-mRNA splicing by antisense oligonucleotides," *Nature Biotech.* (1999) 17:1097-1100.
Schnare, M. et al., "Recognition of CpG DNA is mediated by signaling pathways dependent on the adaptor protein MyD88," *Curr. Biol.* (2000) 10:1139-1142.

(Continued)

*Primary Examiner*—Brian Whiteman
(74) *Attorney, Agent, or Firm*—Knobbe, Martens, Olson & Bear, LLP

(57) ABSTRACT

Antisense compounds, compositions and methods are provided for modulating the expression of MyD88. The compositions comprise antisense compounds, particularly antisense oligonucleotides, targeted to nucleic acids encoding MyD88. Methods of using these compounds for modulation of MyD88 expression and for treatment of diseases associated with expression of MyD88 are provided.

27 Claims, No Drawings

OTHER PUBLICATIONS

Weighardt, H. et al., "Cutting Edge: Myeloid Differentiation Factor 88 Deficiency Improves Resistance Against Sepsis Caused by Polymicrobial Infection," *J. Immunol.* (2002) 169:2823-2827.

Wesche, H. et al., "MyD88: An Adapter That Recruits IRAK to the IL-1 Receptor Complex," *Immunity* (1997) 7:837-847.

Yamamoto, M. et al., "Essential role for TIRAP in activation of the signaling cascade shared by TLR2 and TLR4," *Nature* (2002) 420:324-329.

Branch et al., "A good antisense molecule is hard to find," TIBS (1998) 23:45-50.

Crooke et al., "Basic Principles of Antisense Therapeutics" Antisense Research and Application (1998) Chapter 1:1-50.

Sanghvi et al., "Heterocyclic Base Modifications in Nucleic Acids and Their Applications in Antisense Oligonucleotides" Antisense Research and Applications (1993) pp. 273-288.

* cited by examiner

SEQUENCE LISTING

<160> NUMBER OF SEQ ID NOS: 147

<210> SEQ ID NO 1
<211> LENGTH: 20
<212> TYPE: DNA
<213> ORGANISM: Artificial Sequence
<220> FEATURE:
<223> OTHER INFORMATION: Oligomeric compound

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Oligomeric compound

<400> SEQUENCE: 2
atgcattctg cccccaagga                                              20

<210> SEQ ID NO 3
<211> LENGTH: 5000
<212> TYPE: DNA
<213> ORGANISM: H. sapiens
<220> FEATURE:

<400> SEQUENCE: 3
ccacttgtcc cctcctcgcc atcctcgagg gcaggaccgt atgaacccct cagattcctc      60
cgtggaagaa ctgtggctcc accagatccc aaaaagcaag gcccgtttcc tacaaccccc     120
gaaggagggt cgtcctcact ccgccgccaa cctactagca ccatcaccag accctcgagg     180
gcggtgccgt ggacctctcc agatctcaaa aggcagattc ctacttctta cgcccccac      240 atcacccgcc tcgagacctc aagggtagag gtgggcaccc ccgcctccgc acttttgctc     300
ggggctccag attgtagggc arggcggcgc ttctcggaaa gcgaaagcgg cggggcghgg     360
cgggtgccag gagaaagagg aagcgctggc agacaatgcg acccgaccgc gctgaggctc     420
caggaccgcc cgccatggct gcaggaggtc ccggcgcggg gtctgcggcc ccggtctcct     480
ccacatcctc ccttcccctg gctgctctca acatgcgagt gcggcgccgc ctgtctctgt     540
tcttgaacgt gcggacacag gtggcggccg actggaccgc gctggcggag gagatggact     600 tgagtactt ggagatccgg caactggaga cacaagcgga ccccactggc aggctgctgg      660
acgcctggca gggacgccct ggcgcctctg taggccgact gctcgagctg cttaccaagc     720
tgggctgcga cgacgtgctg ctggagctgg gacccagcat tggtgaggac gtcccccttcc     780 tggcctcgta cctgggggggt gaggaggctg actttccgcg gcctcagcat cctgtctccc     840
atggagagac cccatttcct gcctcggggg cccgaagaag cctgcagagg gagaaccatg     900
cgggtcccgt tccttcttaa taaccggtcg cggttattaa gaaggactgg agaaaggtcc     960
ggataggcgg agatgggaag gaagcagctt aggcagaggc tttcaggtag ggccaggagt    1020
cagaatcagg cttctgtggg ggcatctggg ctgtttcaag tagagcaaca ggacaggtgg    1080
ggcgattgac agtggactgt cttagaaacc tcaagtcctg gggaaatgca gcccttcttt    1140
ctactcactg gcacttacat aatatacatg cataggcgtt ggatacagcc gcccacagac    1200
aggcacacct tgctgagttg gaatcactgc accataacca gtgggtctcc tgagccttc     1260

-continued

```
tggcatgccc agcccttgc tcacatctgc cctggatccc agaagaagca gacctacctt    1320
ggtaccattc ttaggatccc taggaaggga cagagataca aacctgactt tgatggcctt    1380
ccagaaagcc agaacaccac tgacatccct ttgggtcagt tagagccagt gggagctcaa    1440
cttctcagag ccgttgagct tcgcgtggca ccagtgaact ggggaagccc tctagaacaa    1500
cccagccaga ggaggtggga cagcggctgg atcctgactg tgggtaaaga ggtaggcact    1560
cccagggagg ctgctttact ctgtctcttc cccacagagg aggattgcca aaagtatatc    1620
ttgaagcagc agcaggagga ggctgagaag cctttacagg tggccgctgt agacagcagt    1680
gtcccacgga cagcagagct ggcgggcatc accacacttg atgacccct gggtaagggt    1740 ccaatactgt tcccatggga caggtggaat aggacattgt ggtgttaaga gcatgggtgt    1800
ttgaagcaga tgggctgtga gaccttgggc aagtcactta atctttctga gcctcagttt    1860
cctcacctaa gaaatggaga taatagtcct acctctggat tgctgtgaga tgctcatgaa    1920
ataatgtctg tctcgtggtt aatccagagc ttagccctg aggtactcat ctttcctctc    1980
ctggaaaggg cactttctct gaggagtatc atcttgggaa gggtgcaggg cccagggttg    2040
cctaggcagg ggactcttgg ctggatccct cccaagcctt cccatggagc tctgaccacc    2100
acccttgtgc tctgcaccca gggcatatgc ctgagcgttt cgatgccttc atctgctatt    2160
gccccagcga catccagttt gtgcaggaga tgatccggca actggaacag acaaaactatc   2220 gactgaagtt gtgtgtgtct gaccgcgatg tcctgcctgg cacctgtgtc tggtctattg    2280
ctagtgagct catcgaaaag aggttggcta aaggccacg gggtgggtgc gtggatgcat     2340
gaagccctgc cctggggtcc agatactggg catctcctcc tagctgtgca ctgtccagcc    2400
tgggcacagt gggcccttcc tgaagctatt cccaggggat atgctgaact aagttgccac    2460
aggacctgca gcctgcccac tctcccctag gtgccgccgg atggtggtgg ttgtctctga    2520
tgattacctg cagagcaagg aatgtgactt ccagaccaaa tttgcactca gcctctctcc    2580
aggtaagctc aaccctgctc tggcaagaga atgagggaat gtgtaggtgg ggcctctgga    2640
ttgtcagcct tccctcccca aggactgtgg atgcagtacc aaagaactgc tgaagatctc    2700
tgcacacctg agcatgtgtg catgtgtgtg cctttttgtg tgagtgaatg tgtgccaggg    2760
gtacttagat gggggatggc tgttgttaac cctgggggttg aagactgggc ttgtcccacc   2820
atggggcaag ggcctgatgc cagcatggca ccccttggct tgcaggtgcc catcagaagc    2880
gactgatccc catcaagtac aaggcaatga agaaagagtt ccccagcatc ctgaggttca    2940
tcactgtctg cgactacacc aacccctgca ccaaatcttg gttctggact cgccttgcca    3000
aggccttgtc cctgccctga agactgttct gaggccctgg gtgtgtgtgt atctgtctgc    3060
ctgtccatgt acttctgccc tgcctcctcc tttcgttgta ggaggaatct gtgctctact    3120
tacctctcaa ttcctggaga tgccaacttc acagacacgt ctgcagcagc tggacatcac    3180
atttcatgtc ctgcatggaa ccagtggctg tgagtggcat gtccacttgc tggattatca    3240
gccaggacac tatagaacag gaccagctga gactaagaag gaccagcaga gccagctcag    3300
ctctgagcca ttcacacatc ttcaccctca gtttcctcac ttgaggagtg ggatggggag    3360
aacagagagt agctgtgttt gaatccctgt aggaaatggt gaagcatagc tctgggtctc    3420
ctgggggaga ccaggcttgg ctgcgggaga gctggctgtt gctggactac atgctggcca    3480
ctgctgtgac cacgacactg ctggggcagc ttcttccaca gtgatgccta ctgatgcttc    3540
agtgcctctg cacaccgccc attccacttc ctccttcccc acagggcagg tggggaagca    3600
gtttggccca gcccaaggag accccacctt gagccttatt tcctaatggg tccacctctc    3660
```

```
atctgcatct tcacacctc ccagcttctg cccaaccttc agcagtgaca agtccccaag    3720
agactcgcct gagcagcttg ggctgctttt catttccacc tgtcaggatg cctgtggtca    3780
tgctctcagc tccacctggc atgagaaggg atcctggcct ctggcatatt catcaagtat    3840
gagttctggg gatgagtcac tgtaatgatg tgagcaggga gccttcctcc ctgggccacc    3900
tgcagagagc tttcccacca actttgtacc ttgattgcct tacaaagtta tttgtttaca    3960
aacagcgacc atataaaagc ctcctgcccc aaagcttgtg ggcacatggg cacatacaga    4020
ctcacataca gacacacaca tatatgtaca gacatgtact ctcacacaca caggcaccag    4080
catacacacg tttttctagg tacagctccc aggaacagct aggtgggaaa gtcccatcac    4140
tgagggagcc taaccatgtc cctgaacaaa aattgggcac tcatctattc ctttctctt    4200 gtgtccctac tcattgaaac caaactctgg aaaggaccca atgtaccagt atttatacct    4260
ctaatgaagc acagagagag gaagagagct gcttaaactc acacaacaat gaactgcaga    4320
cacagctgtt ctctccctct ctccttccca gagcaattta tactttaccc tcaggctgtc    4380
ctctggggag aaggtgccat ggtcttaggt gtctgtgccc caggacagac cctaggaccc    4440
taaatccaat agaaaatgca tatctttgct ccactttcag ccaggctgga gcaaggtacc    4500
ttttcttagg atcttgggag ggaatggatg cccctctctg catgatcttg ttgaggcatt    4560
tagctgccat gcacctgtcc ccctttaata ctgggcattt taaagccatc tcaagaggca    4620
tcttctacat gttttgtacg cattaaaata atttcaaaga tatctgagaa aagccgatat    4680
ttgccattct tcctatatcc tggaatatat cttgcatcct gagtttataa taataaataa    4740
tattctacct tggaaacttg tgtgtgtgtt gagtggaaga ggtttggaag cagtaatgtg    4800
ggtaagagaa gctggtccac tgggtgggtt ccagcctgga tttggcacgg gcttcctgaa    4860
agctgggccc cctcctcaca ggttcagtcc taagcagggc tgcaggcaga accaggaata    4920
ctgacctcag ctacagacac tcaggagact gcccttctct ggccatgtcc aatctttct    4980 tggttgtgcc atgctcctgg                                                5000

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
gggctgcttt tcatttccac                                                  20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
aggccaggat cccttctcat                                                  20

<210> SEQ ID NO 6
<211> LENGTH: 26
<212> TYPE: DNA
<213> ORGANISM: Artificial Sequence
<220> FEATURE:
<223> OTHER INFORMATION: PCR Probe
```

<400> SEQUENCE: 6
aggatgcctg tggtcatgct ctcagc    26

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc    19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc    20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc    20

<210> SEQ ID NO 10
<211> LENGTH: 959
<212> TYPE: DNA
<213> ORGANISM: H. sapiens
<220> FEATURE:

<400> SEQUENCE: 10
caagggtaga ggtgggcacc cccgcctccg cactttttgct cggggctcca gattgtaggg    60
cagggcggcg cttctcggaa agcgaaagcc ggcggggcgg ggcgggtgcc gcaggagaaa   120
gaggaagcgc tggcagacaa tgcgacccga ccgcgctgag gctccaggac cgcccgccat   180
ggctgcagga ggtcccggcg cggggtctgc ggccccggtc tcctccacat cctcccttcc   240
cctggctgct ctcaacatgc gagtgcggcg ccgcctgtct ctgttcttga acgtgcggac   300
acaggtggcg gccgactgga ccgcgctggc ggaggagatg gactttgagt acttggagat   360
ccggcaactg gagacacaag cggaccccac tggcaggctg ctggacgcct ggcagggacg   420
ccctggcgcc tctgtaggcc gactgctcga gctgcttacc aagctgggcc gcgacgacgt   480
gctgctggag ctgggaccca gcattgagga ggattgccaa aagtatatct tgaagcagca   540
gcaggaggag gctgagaagc tttacaggtg gccgctgtag acagcagtgt cccacggaca   600
gcagagctgg cgggcatcac cacacttgat gaccccctgg ggcatatgcc tgagcgtttc   660
gatgccttca tctgctattg ccccagcgac atccagtttg tgcaggagat gatccggcaa   720
ctggaacaga caaactatcg actgaagttg tgtgtgtctg accgcgatgt cctgcctggc   780
acctgtgtct ggtctattgc tagtgagctc atcgaaaaga ggtgccgccg gatggtggtg   840
gttgtctctg atgattacct gcagagcaag ggaatgtgac ttccagacca aatttgcact   900
cagcctctct ccaggtgscc atcagaagcg actgatcccc atcaagtaca aggcaatga    959

<210> SEQ ID NO 11
<211> LENGTH: 951
<212> TYPE: DNA
<213> ORGANISM: H. sapiens
<220> FEATURE:
<220> FEATURE:
<221> NAME/KEY: CDS
<222> LOCATION: (61)...(951)

<400> SEQUENCE: 11
aagaggaagc gctggcagac aatgcgaccc gaccgcgctg aggctccagg accgccgcc    60 atg gct gca gga ggt ccc ggc gcg ggg tct gcg gcc ccg gtc tcc tcc    108
Met Ala Ala Gly Gly Pro Gly Ala Gly Ser Ala Ala Pro Val Ser Ser
1               5                   10                  15 aca tcc tcc ctt ccc ctg gct gct ctc aac atg cga gtg cgg cgc cgc    156
Thr Ser Ser Leu Pro Leu Ala Ala Leu Asn Met Arg Val Arg Arg Arg
            20                  25                  30 ctg tct ctg ttc ttg aac gtg cgg aca cag gtg gcg gcc gac tgg acc    204
Leu Ser Leu Phe Leu Asn Val Arg Thr Gln Val Ala Ala Asp Trp Thr
        35                  40                  45 gcg ctg gcg gag gag atg gac ttt gag tac ttg gag atc cgg caa ctg    252
Ala Leu Ala Glu Glu Met Asp Phe Glu Tyr Leu Glu Ile Arg Gln Leu
    50                  55                  60 gag aca caa gcg gac ccc act ggc agg ctg ctg gac gcc tgg cag gga    300
Glu Thr Gln Ala Asp Pro Thr Gly Arg Leu Leu Asp Ala Trp Gln Gly
65                  70                  75                  80 cgc cct ggc gcc tct gta ggc cga ctg ctc gag ctg ctt acc aag ctg    348
Arg Pro Gly Ala Ser Val Gly Arg Leu Leu Glu Leu Leu Thr Lys Leu
                85                  90                  95 ggc cgc gac gac gtg ctg ctg gag ctg gga ccc agc att gag gag gat    396
Gly Arg Asp Asp Val Leu Leu Glu Leu Gly Pro Ser Ile Glu Glu Asp
            100                 105                 110 tgc caa aag tat atc ttg aag cag cag cag gag gag gct gag aag cct    444
Cys Gln Lys Tyr Ile Leu Lys Gln Gln Gln Glu Glu Ala Glu Lys Pro
        115                 120                 125 tta cag gtg gcc gct gta gac agc agt gtc cca cgg aca gca gag ctg    492
Leu Gln Val Ala Ala Val Asp Ser Ser Val Pro Arg Thr Ala Glu Leu
    130                 135                 140 gcg ggc atc acc aca ctt gat gac ccc ctg ggg cat atg cct gag cgt    540
Ala Gly Ile Thr Thr Leu Asp Asp Pro Leu Gly His Met Pro Glu Arg
145                 150                 155                 160 ttc gat gcc ttc atc tgc tat tgc ccc agc gac atc cag ttt gtg cag    588
Phe Asp Ala Phe Ile Cys Tyr Cys Pro Ser Asp Ile Gln Phe Val Gln
                165                 170                 175 gag atg atc cgg caa ctg gaa cag aca aac tat cga ctg aag ttg tgt    636
Glu Met Ile Arg Gln Leu Glu Gln Thr Asn Tyr Arg Leu Lys Leu Cys
            180                 185                 190 gtg tct gac cgc gat gtc ctg cct ggc acc tgt gtc tgg tct att gct    684
Val Ser Asp Arg Asp Val Leu Pro Gly Thr Cys Val Trp Ser Ile Ala
        195                 200                 205 agt gag ctc atc gaa aag agg tgc cgc cgg atg gtg gtg gtt gtc tct    732
Ser Glu Leu Ile Glu Lys Arg Cys Arg Arg Met Val Val Val Val Ser
    210                 215                 220 gat gat tac ctg cag agc aag gaa tgt gac ttc cag acc aaa ttt gca    780
Asp Asp Tyr Leu Gln Ser Lys Glu Cys Asp Phe Gln Thr Lys Phe Ala
225                 230                 235                 240 ctc agc ctc tct cca ggt gcc cat cag aag cga ctg atc ccc atc aag    828
Leu Ser Leu Ser Pro Gly Ala His Gln Lys Arg Leu Ile Pro Ile Lys
                245                 250                 255

```
tac aag gca atg aag aaa gag ttc ccc agc atc ctg agg ttc atc act    876
Tyr Lys Ala Met Lys Lys Glu Phe Pro Ser Ile Leu Arg Phe Ile Thr
            260                 265                 270 gtc tgc gac tac acc aac ccc tgc acc aaa tct tgg ttc tgg act cgc    924
Val Cys Asp Tyr Thr Asn Pro Cys Thr Lys Ser Trp Phe Trp Thr Arg
        275                 280                 285 ctt gcc aag gcc ttg tcc ctg ccc tga                                951
Leu Ala Lys Ala Leu Ser Leu Pro
    290                 295

<210> SEQ ID NO 12
<211> LENGTH: 20
<212> TYPE: DNA
<213> ORGANISM: Artificial Sequence
<220> FEATURE:
<223> OTHER INFORMATION: Oligomeric compound

<400> SEQUENCE: 12
gtcgcattgt ctgccagcgc                                               20

<210> SEQ ID NO 13
<211> LENGTH: 20
<212> TYPE: DNA
<213> ORGANISM: Artificial Sequence
<220> FEATURE:
<223> OTHER INFORMATION: Oligomeric compound

<400> SEQUENCE: 13
gtcgggtcgc attgtctgcc                                               20

<210> SEQ ID NO 14
<211> LENGTH: 20
<212> TYPE: DNA
<213> ORGANISM: Artificial Sequence
<220> FEATURE:
<223> OTHER INFORMATION: Oligomeric compound

<400> SEQUENCE: 14
cctggagcct cagcgcggtc                                               20

<210> SEQ ID NO 15
<211> LENGTH: 20
<212> TYPE: DNA
<213> ORGANISM: Artificial Sequence
<220> FEATURE:
<223> OTHER INFORMATION: Oligomeric compound

<400> SEQUENCE: 15
gcggtcctgg agcctcagcg                                               20

<210> SEQ ID NO 16
<211> LENGTH: 20
<212> TYPE: DNA
<213> ORGANISM: Artificial Sequence
<220> FEATURE:
<223> OTHER INFORMATION: Oligomeric compound

<400> SEQUENCE: 16
ccatggcggg cggtcctgga                                               20

<210> SEQ ID NO 17
<211> LENGTH: 20
<212> TYPE: DNA
<213> ORGANISM: Artificial Sequence
<220> FEATURE:
```

-continued

<223> OTHER INFORMATION: Oligomeric compound

<400> SEQUENCE: 17
tcctgcagcc atggcgggcg                                                20

<210> SEQ ID NO 18
<211> LENGTH: 20
<212> TYPE: DNA
<213> ORGANISM: Artificial Sequence
<220> FEATURE:
<223> OTHER INFORMATION: Oligomeric compound

<400> SEQUENCE: 18
cgggacctcc tgcagccatg                                                20

<210> SEQ ID NO 19
<211> LENGTH: 20
<212> TYPE: DNA
<213> ORGANISM: Artificial Sequence
<220> FEATURE:
<223> OTHER INFORMATION: Oligomeric compound

<400> SEQUENCE: 19
catgttgaga gcagccaggg                                                20

<210> SEQ ID NO 20
<211> LENGTH: 20
<212> TYPE: DNA
<213> ORGANISM: Artificial Sequence
<220> FEATURE:
<223> OTHER INFORMATION: Oligomeric compound

<400> SEQUENCE: 20
cactcgcatg ttgagagcag                                                20

<210> SEQ ID NO 21
<211> LENGTH: 20
<212> TYPE: DNA
<213> ORGANISM: Artificial Sequence
<220> FEATURE:
<223> OTHER INFORMATION: Oligomeric compound

<400> SEQUENCE: 21
cgttcaagaa cagagacagg                                                20

<210> SEQ ID NO 22
<211> LENGTH: 20
<212> TYPE: DNA
<213> ORGANISM: Artificial Sequence
<220> FEATURE:
<223> OTHER INFORMATION: Oligomeric compound

<400> SEQUENCE: 22
tgtccgcacg ttcaagaaca                                                20

<210> SEQ ID NO 23
<211> LENGTH: 20
<212> TYPE: DNA
<213> ORGANISM: Artificial Sequence
<220> FEATURE:
<223> OTHER INFORMATION: Oligomeric compound

<400> SEQUENCE: 23
tactcaaagt ccatctcctc                                                20

```
<210> SEQ ID NO 24
<211> LENGTH: 20
<212> TYPE: DNA
<213> ORGANISM: Artificial Sequence
<220> FEATURE:
<223> OTHER INFORMATION: Oligomeric compound

<400> SEQUENCE: 24
tccaagtact caaagtccat                                                   20

<210> SEQ ID NO 25
<211> LENGTH: 20
<212> TYPE: DNA
<213> ORGANISM: Artificial Sequence
<220> FEATURE:
<223> OTHER INFORMATION: Oligomeric compound

<400> SEQUENCE: 25
ttgccggatc tccaagtact                                                   20

<210> SEQ ID NO 26
<211> LENGTH: 20
<212> TYPE: DNA
<213> ORGANISM: Artificial Sequence
<220> FEATURE:
<223> OTHER INFORMATION: Oligomeric compound

<400> SEQUENCE: 26
gtctccagtt gccggatctc                                                   20

<210> SEQ ID NO 27
<211> LENGTH: 20
<212> TYPE: DNA
<213> ORGANISM: Artificial Sequence
<220> FEATURE:
<223> OTHER INFORMATION: Oligomeric compound

<400> SEQUENCE: 27
gtccagcagc ctgccagtgg                                                   20

<210> SEQ ID NO 28
<211> LENGTH: 20
<212> TYPE: DNA
<213> ORGANISM: Artificial Sequence
<220> FEATURE:
<223> OTHER INFORMATION: Oligomeric compound

<400> SEQUENCE: 28
cagtcggcct acagaggcgc                                                   20

<210> SEQ ID NO 29
<211> LENGTH: 20
<212> TYPE: DNA
<213> ORGANISM: Artificial Sequence
<220> FEATURE:
<223> OTHER INFORMATION: Oligomeric compound

<400> SEQUENCE: 29
cagctcgagc agtcggccta                                                   20

<210> SEQ ID NO 30
<211> LENGTH: 20
<212> TYPE: DNA
<213> ORGANISM: Artificial Sequence
<220> FEATURE:
<223> OTHER INFORMATION: Oligomeric compound
```

```
<400> SEQUENCE: 30
ggtaagcagc tcgagcagtc                                              20

<210> SEQ ID NO 31
<211> LENGTH: 20
<212> TYPE: DNA
<213> ORGANISM: Artificial Sequence
<220> FEATURE:
<223> OTHER INFORMATION: Oligomeric compound

<400> SEQUENCE: 31
gcccagcttg gtaagcagct                                              20

<210> SEQ ID NO 32
<211> LENGTH: 20
<212> TYPE: DNA
<213> ORGANISM: Artificial Sequence
<220> FEATURE:
<223> OTHER INFORMATION: Oligomeric compound

<400> SEQUENCE: 32
gtcgcggccc agcttggtaa                                              20

<210> SEQ ID NO 33
<211> LENGTH: 20
<212> TYPE: DNA
<213> ORGANISM: Artificial Sequence
<220> FEATURE:
<223> OTHER INFORMATION: Oligomeric compound

<400> SEQUENCE: 33
ctcaatgctg ggtcccagct                                              20

<210> SEQ ID NO 34
<211> LENGTH: 20
<212> TYPE: DNA
<213> ORGANISM: Artificial Sequence
<220> FEATURE:
<223> OTHER INFORMATION: Oligomeric compound

<400> SEQUENCE: 34
tggcaatcct cctcaatgct                                              20

<210> SEQ ID NO 35
<211> LENGTH: 20
<212> TYPE: DNA
<213> ORGANISM: Artificial Sequence
<220> FEATURE:
<223> OTHER INFORMATION: Oligomeric compound

<400> SEQUENCE: 35
ctgcttcaag atatactttt                                              20

<210> SEQ ID NO 36
<211> LENGTH: 20
<212> TYPE: DNA
<213> ORGANISM: Artificial Sequence
<220> FEATURE:
<223> OTHER INFORMATION: Oligomeric compound

<400> SEQUENCE: 36
agcctcctcc tgctgctgct                                              20

<210> SEQ ID NO 37
<211> LENGTH: 20
```

```
<212> TYPE: DNA
<213> ORGANISM: Artificial Sequence
<220> FEATURE:
<223> OTHER INFORMATION: Oligomeric compound

<400> SEQUENCE: 37
aggcttctca gcctcctcct                                          20

<210> SEQ ID NO 38
<211> LENGTH: 20
<212> TYPE: DNA
<213> ORGANISM: Artificial Sequence
<220> FEATURE:
<223> OTHER INFORMATION: Oligomeric compound

<400> SEQUENCE: 38
gccacctgta aaggcttctc                                          20

<210> SEQ ID NO 39
<211> LENGTH: 20
<212> TYPE: DNA
<213> ORGANISM: Artificial Sequence
<220> FEATURE:
<223> OTHER INFORMATION: Oligomeric compound

<400> SEQUENCE: 39
ctgctgtcta cagcggccac                                          20

<210> SEQ ID NO 40
<211> LENGTH: 20
<212> TYPE: DNA
<213> ORGANISM: Artificial Sequence
<220> FEATURE:
<223> OTHER INFORMATION: Oligomeric compound

<400> SEQUENCE: 40
gctgtccgtg ggacactgct                                          20

<210> SEQ ID NO 41
<211> LENGTH: 20
<212> TYPE: DNA
<213> ORGANISM: Artificial Sequence
<220> FEATURE:
<223> OTHER INFORMATION: Oligomeric compound

<400> SEQUENCE: 41
cagctctgct gtccgtggga                                          20

<210> SEQ ID NO 42
<211> LENGTH: 20
<212> TYPE: DNA
<213> ORGANISM: Artificial Sequence
<220> FEATURE:
<223> OTHER INFORMATION: Oligomeric compound

<400> SEQUENCE: 42
atcaagtgtg gtgatgcccg                                          20

<210> SEQ ID NO 43
<211> LENGTH: 20
<212> TYPE: DNA
<213> ORGANISM: Artificial Sequence
<220> FEATURE:
<223> OTHER INFORMATION: Oligomeric compound

<400> SEQUENCE: 43
```
cgctcaggca tatgcccag                                        20

<210> SEQ ID NO 44
<211> LENGTH: 20
<212> TYPE: DNA
<213> ORGANISM: Artificial Sequence
<220> FEATURE:
<223> OTHER INFORMATION: Oligomeric compound
<400> SEQUENCE: 44
caatagcaga tgaaggcatc                                       20

<210> SEQ ID NO 45
<211> LENGTH: 20
<212> TYPE: DNA
<213> ORGANISM: Artificial Sequence
<220> FEATURE:
<223> OTHER INFORMATION: Oligomeric compound
<400> SEQUENCE: 45
gatcatctcc tgcacaaact                                       20

<210> SEQ ID NO 46
<211> LENGTH: 20
<212> TYPE: DNA
<213> ORGANISM: Artificial Sequence
<220> FEATURE:
<223> OTHER INFORMATION: Oligomeric compound
<400> SEQUENCE: 46
tgccggatca tctcctgcac                                       20

<210> SEQ ID NO 47
<211> LENGTH: 20
<212> TYPE: DNA
<213> ORGANISM: Artificial Sequence
<220> FEATURE:
<223> OTHER INFORMATION: Oligomeric compound
<400> SEQUENCE: 47
ccagttgccg gatcatctcc                                       20

<210> SEQ ID NO 48
<211> LENGTH: 20
<212> TYPE: DNA
<213> ORGANISM: Artificial Sequence
<220> FEATURE:
<223> OTHER INFORMATION: Oligomeric compound
<400> SEQUENCE: 48
cgatagtttg tctgttccag                                       20

<210> SEQ ID NO 49
<211> LENGTH: 20
<212> TYPE: DNA
<213> ORGANISM: Artificial Sequence
<220> FEATURE:
<223> OTHER INFORMATION: Oligomeric compound
<400> SEQUENCE: 49
ttcagtcgat agtttgtctg                                       20

<210> SEQ ID NO 50
<211> LENGTH: 20
<212> TYPE: DNA
<213> ORGANISM: Artificial Sequence -continued
<220> FEATURE:
<223> OTHER INFORMATION: Oligomeric compound

<400> SEQUENCE: 50
ggtcagacac acacaacttc                                           20

<210> SEQ ID NO 51
<211> LENGTH: 20
<212> TYPE: DNA
<213> ORGANISM: Artificial Sequence
<220> FEATURE:
<223> OTHER INFORMATION: Oligomeric compound

<400> SEQUENCE: 51
ggacatcgcg gtcagacaca                                           20

<210> SEQ ID NO 52
<211> LENGTH: 20
<212> TYPE: DNA
<213> ORGANISM: Artificial Sequence
<220> FEATURE:
<223> OTHER INFORMATION: Oligomeric compound

<400> SEQUENCE: 52
tagaccagac acaggtgcca                                           20

<210> SEQ ID NO 53
<211> LENGTH: 20
<212> TYPE: DNA
<213> ORGANISM: Artificial Sequence
<220> FEATURE:
<223> OTHER INFORMATION: Oligomeric compound

<400> SEQUENCE: 53
tcactagcaa tagaccagac                                           20

<210> SEQ ID NO 54
<211> LENGTH: 20
<212> TYPE: DNA
<213> ORGANISM: Artificial Sequence
<220> FEATURE:
<223> OTHER INFORMATION: Oligomeric compound

<400> SEQUENCE: 54
cgatgagctc actagcaata                                           20

<210> SEQ ID NO 55
<211> LENGTH: 20
<212> TYPE: DNA
<213> ORGANISM: Artificial Sequence
<220> FEATURE:
<223> OTHER INFORMATION: Oligomeric compound

<400> SEQUENCE: 55
cacctctttt cgatgagctc                                           20

<210> SEQ ID NO 56
<211> LENGTH: 20
<212> TYPE: DNA
<213> ORGANISM: Artificial Sequence
<220> FEATURE:
<223> OTHER INFORMATION: Oligomeric compound

<400> SEQUENCE: 56
atccggcggc acctcttttc                                           20

<210> SEQ ID NO 57
<211> LENGTH: 20
<212> TYPE: DNA
<213> ORGANISM: Artificial Sequence
<220> FEATURE:
<223> OTHER INFORMATION: Oligomeric compound

<400> SEQUENCE: 57
tcatcagaga caaccaccac                                         20

<210> SEQ ID NO 58
<211> LENGTH: 20
<212> TYPE: DNA
<213> ORGANISM: Artificial Sequence
<220> FEATURE:
<223> OTHER INFORMATION: Oligomeric compound

<400> SEQUENCE: 58
aggtaatcat cagagacaac                                         20

<210> SEQ ID NO 59
<211> LENGTH: 20
<212> TYPE: DNA
<213> ORGANISM: Artificial Sequence
<220> FEATURE:
<223> OTHER INFORMATION: Oligomeric compound

<400> SEQUENCE: 59
tctgcaggta atcatcagag                                         20

<210> SEQ ID NO 60
<211> LENGTH: 20
<212> TYPE: DNA
<213> ORGANISM: Artificial Sequence
<220> FEATURE:
<223> OTHER INFORMATION: Oligomeric compound

<400> SEQUENCE: 60
cttgctctgc aggtaatcat                                         20

<210> SEQ ID NO 61
<211> LENGTH: 20
<212> TYPE: DNA
<213> ORGANISM: Artificial Sequence
<220> FEATURE:
<223> OTHER INFORMATION: Oligomeric compound

<400> SEQUENCE: 61
aagtcacatt ccttgctctg                                         20

<210> SEQ ID NO 62
<211> LENGTH: 20
<212> TYPE: DNA
<213> ORGANISM: Artificial Sequence
<220> FEATURE:
<223> OTHER INFORMATION: Oligomeric compound

<400> SEQUENCE: 62
tctggaagtc acattccttg                                         20

<210> SEQ ID NO 63
<211> LENGTH: 20
<212> TYPE: DNA
<213> ORGANISM: Artificial Sequence
<220> FEATURE:
<223> OTHER INFORMATION: Oligomeric compound

```
<400> SEQUENCE: 63
aatttggtct ggaagtcaca                                              20

<210> SEQ ID NO 64
<211> LENGTH: 20
<212> TYPE: DNA
<213> ORGANISM: Artificial Sequence
<220> FEATURE:
<223> OTHER INFORMATION: Oligomeric compound

<400> SEQUENCE: 64
gtgcaaattt ggtctggaag                                              20

<210> SEQ ID NO 65
<211> LENGTH: 20
<212> TYPE: DNA
<213> ORGANISM: Artificial Sequence
<220> FEATURE:
<223> OTHER INFORMATION: Oligomeric compound

<400> SEQUENCE: 65
agaggctgag tgcaaatttg                                              20

<210> SEQ ID NO 66
<211> LENGTH: 20
<212> TYPE: DNA
<213> ORGANISM: Artificial Sequence
<220> FEATURE:
<223> OTHER INFORMATION: Oligomeric compound

<400> SEQUENCE: 66
cctggagaga ggctgagtgc                                              20

<210> SEQ ID NO 67
<211> LENGTH: 20
<212> TYPE: DNA
<213> ORGANISM: Artificial Sequence
<220> FEATURE:
<223> OTHER INFORMATION: Oligomeric compound

<400> SEQUENCE: 67
tgggcacctg gagagaggct                                              20

<210> SEQ ID NO 68
<211> LENGTH: 20
<212> TYPE: DNA
<213> ORGANISM: Artificial Sequence
<220> FEATURE:
<223> OTHER INFORMATION: Oligomeric compound

<400> SEQUENCE: 68
gtcgcttctg atgggcacct                                              20

<210> SEQ ID NO 69
<211> LENGTH: 20
<212> TYPE: DNA
<213> ORGANISM: Artificial Sequence
<220> FEATURE:
<223> OTHER INFORMATION: Oligomeric compound

<400> SEQUENCE: 69
tcattgcctt gtacttgatg                                              20

<210> SEQ ID NO 70
```

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 70
gtgatgaacc tcaggatgct                                              20

<210> SEQ ID NO 71
<211> LENGTH: 20
<212> TYPE: DNA
<213> ORGANISM: Artificial Sequence
<220> FEATURE:
<223> OTHER INFORMATION: Oligomeric compound

<400> SEQUENCE: 71
tagtcgcaga cagtgatgaa                                              20

<210> SEQ ID NO 72
<211> LENGTH: 20
<212> TYPE: DNA
<213> ORGANISM: Artificial Sequence
<220> FEATURE:
<223> OTHER INFORMATION: Oligomeric compound

<400> SEQUENCE: 72
tggtgtagtc gcagacagtg                                              20

<210> SEQ ID NO 73
<211> LENGTH: 20
<212> TYPE: DNA
<213> ORGANISM: Artificial Sequence
<220> FEATURE:
<223> OTHER INFORMATION: Oligomeric compound

<400> SEQUENCE: 73
tccagaacca agatttggtg                                              20

<210> SEQ ID NO 74
<211> LENGTH: 20
<212> TYPE: DNA
<213> ORGANISM: Artificial Sequence
<220> FEATURE:
<223> OTHER INFORMATION: Oligomeric compound

<400> SEQUENCE: 74
aggcgagtcc agaaccaaga                                              20

<210> SEQ ID NO 75
<211> LENGTH: 20
<212> TYPE: DNA
<213> ORGANISM: Artificial Sequence
<220> FEATURE:
<223> OTHER INFORMATION: Oligomeric compound

<400> SEQUENCE: 75
tggcaaggcg agtccagaac                                              20

<210> SEQ ID NO 76
<211> LENGTH: 20
<212> TYPE: DNA
<213> ORGANISM: Artificial Sequence
<220> FEATURE:
<223> OTHER INFORMATION: Oligomeric compound

<400> SEQUENCE: 76
```
aggccttggc aaggcgagtc                                              20

<210> SEQ ID NO 77
<211> LENGTH: 20
<212> TYPE: DNA
<213> ORGANISM: Artificial Sequence
<220> FEATURE:
<223> OTHER INFORMATION: Oligomeric compound

<400> SEQUENCE: 77
gggacaaggc cttggcaagg                                              20

<210> SEQ ID NO 78
<211> LENGTH: 20
<212> TYPE: DNA
<213> ORGANISM: Artificial Sequence
<220> FEATURE:
<223> OTHER INFORMATION: Oligomeric compound

<400> SEQUENCE: 78
gggtgcccac ctctaccctt                                              20

<210> SEQ ID NO 79
<211> LENGTH: 20
<212> TYPE: DNA
<213> ORGANISM: Artificial Sequence
<220> FEATURE:
<223> OTHER INFORMATION: Oligomeric compound

<400> SEQUENCE: 79
tctggagccc cgagcaaaag                                              20

<210> SEQ ID NO 80
<211> LENGTH: 20
<212> TYPE: DNA
<213> ORGANISM: Artificial Sequence
<220> FEATURE:
<223> OTHER INFORMATION: Oligomeric compound

<400> SEQUENCE: 80
tacaatctgg agccccgagc                                              20

<210> SEQ ID NO 81
<211> LENGTH: 20
<212> TYPE: DNA
<213> ORGANISM: Artificial Sequence
<220> FEATURE:
<223> OTHER INFORMATION: Oligomeric compound

<400> SEQUENCE: 81
gccctgccct acaatctgga                                              20

<210> SEQ ID NO 82
<211> LENGTH: 20
<212> TYPE: DNA
<213> ORGANISM: Artificial Sequence
<220> FEATURE:
<223> OTHER INFORMATION: Oligomeric compound

<400> SEQUENCE: 82
acgtcctcac caatgctggg                                              20

<210> SEQ ID NO 83
<211> LENGTH: 20
<212> TYPE: DNA

-continued

```
<213> ORGANISM: Artificial Sequence
<220> FEATURE:
<223> OTHER INFORMATION: Oligomeric compound

<400> SEQUENCE: 83
tccgcctatc cggacctttc                                               20

<210> SEQ ID NO 84
<211> LENGTH: 20
<212> TYPE: DNA
<213> ORGANISM: Artificial Sequence
<220> FEATURE:
<223> OTHER INFORMATION: Oligomeric compound

<400> SEQUENCE: 84
aaacagccca gatgccccca                                               20

<210> SEQ ID NO 85
<211> LENGTH: 20
<212> TYPE: DNA
<213> ORGANISM: Artificial Sequence
<220> FEATURE:
<223> OTHER INFORMATION: Oligomeric compound

<400> SEQUENCE: 85
cctgtcctgt tgctctactt                                               20

<210> SEQ ID NO 86
<211> LENGTH: 20
<212> TYPE: DNA
<213> ORGANISM: Artificial Sequence
<220> FEATURE:
<223> OTHER INFORMATION: Oligomeric compound

<400> SEQUENCE: 86
tctagccaac ctcttttcga                                               20

<210> SEQ ID NO 87
<211> LENGTH: 20
<212> TYPE: DNA
<213> ORGANISM: Artificial Sequence
<220> FEATURE:
<223> OTHER INFORMATION: Oligomeric compound

<400> SEQUENCE: 87
ttgagcttac ctggagagag                                               20

<210> SEQ ID NO 88
<211> LENGTH: 20
<212> TYPE: DNA
<213> ORGANISM: Artificial Sequence
<220> FEATURE:
<223> OTHER INFORMATION: Oligomeric compound

<400> SEQUENCE: 88
gctcaggtgt gcagagatct                                               20

<210> SEQ ID NO 89
<211> LENGTH: 20
<212> TYPE: DNA
<213> ORGANISM: Artificial Sequence
<220> FEATURE:
<223> OTHER INFORMATION: Oligomeric compound

<400> SEQUENCE: 89
tgatgggcac ctgcaagcca                                               20
```

<210> SEQ ID NO 90
<211> LENGTH: 2682
<212> TYPE: DNA
<213> ORGANISM: H. sapiens

<400> SEQUENCE: 90

```
gggtagaccc acgagtccgc ccacgggtct gcatggctgc aggaggtccc ggcgcgggt      60
ctgcggcccc ggtctcctcc acatcctccc ttcccctggc tgctctcaac atgcgagtgc    120
ggcgccgcct gtctctgttc ttgaacgtgc ggacacaggt ggcggccgac tggaccgcgc    180
tggcggagga gatggacttt gagtacttgg agatccggca actggagaca caagcggacc    240
ccactggcag gctgctggac gcctggcagg gacgccctgg cgcctctgta ggccgactgc    300
tcgagctgct taccaagctg ggctgcgacg acgtgctgct ggagctggga cccagcattg    360
aggaggattg ccaaaagtat atcttgaagc agcagcagga ggaggctgag aagcctttac    420
aggtggccgc tgtagacagc agtgtcccac ggacagcaga gctggcgggc atcaccacac    480
ttgatgaccc cctggggcat atgcctgagc gtttcgatgc cttcatctgc tattgcccca    540
gcgacatcca gtttgtgcag gagatgatcc ggcaactgga cagacaaac tatcgactga    600
agttgtgtgt gtctgaccgc gatgtcctgc ctggcacctg tgtctggtct attgctagtg    660
agctcatcga aaagaggtgc cgccggatgg tggtggttgt ctctgatgat tacctgcaga    720
gcaaggaatg tgacttccag accaaatttg cactcagcct ctctccaggt gcccatcaga    780
agcgactgat ccccatcaag tacaaggcaa tgaagaaaga gttccccagc atcctgaggt    840
tcatcactgt ctgcgactac accaacccct gcaccaaatc ttggttctgg actcgccttg    900
ccaaggcctt gtccctgccc tgaagactgt tctgaggccc tgggtgtgtg tgtatctgtc    960
tgcctgtcca tgtacttctg ccctgcctcc tcctttcgtt gtaggaggaa tctgtgctct   1020
acttacctct caattcctgg agatgccaac ttcacagaca cgtctgcagc agctggacat   1080
cacatttcat gtcctgcatg gaaccagtgg ctgtgagtgg catgtccact tgctggatta   1140
tcagccagga cactatagaa caggaccagc tgagactaag aaggaccagc agagccagct   1200
cagctctgag ccattcacac atcttcaccc tcagtttcct cacttgagga gtgggatggg   1260
gagaacagag agtagctgtg tttgaatccc tgtaggaaat ggtgaagcat agctctgggt   1320
ctcctggggg agaccaggct tggctgcggg agagctggct gttgctggac tacatgctgg   1380
ccactgctgt gaccacgaca ctgctggggc agcttcttcc acagtgatgc ctactgatgc   1440
ttcagtgcct ctgcacaccg cccattccac ttcctccttc cccacagggc aggtggggaa   1500
gcagtttggc ccagcccaag gagacccac cttgagcctt atttcctaat gggtccacct   1560
ctcatctgca tctttcacac ctcccagctt ctgcccaacc ttcagcagtg acaagtcccc   1620
aagagactcg cctgagcagc ttgggctgct tttcatttcc acctgtcagg atgcctgtgg   1680
tcatgctctc agctccacct ggcatgagaa gggatcctgg cctctggcat attcatcaag   1740
tatgagttct ggggatgagt cactgtaatg atgtgagcag ggagccttcc tccctgggcc   1800
acctgcagag agctttccca ccaactttgt accttgattg ccttacaaag ttatttgttt   1860
acaaacagcg accatataaa agcctcctgc cccaaagctt gtgggcacat gggcacatac   1920
agactcacat acagacacac acatatatgt acagacatgt actctcacac acacaggcac   1980
cagcatacac acgttttttct aggtacagct cccaggaaca gctaggtggg aaagtcccat   2040
cactgaggga gcctaaccat gtccctgaac aaaaattggg cactcatcta ttccttttct   2100
```

-continued

```
cttgtgtccc tactcattga aaccaaactc tggaaaggac ccaatgtacc agtatttata    2160
cctctaatga agcacagaga gaggaagaga gctgcttaaa ctcacacaac aatgaactgc    2220
agacacagct gttctctccc tctctccttc ccagagcaat ttatacttta ccctcaggct    2280
gtcctctggg gagaaggtgc catggtctta ggtgtctgtg ccccaggaca gaccctagga    2340
ccctaaatcc aatagaaaat gcatatcttt gctccacttt cagccaggct ggagcaaggt    2400 acctttctt aggatcttgg gagggaatgg atgcccctct ctgcatgatc ttgttgaggc     2460
atttagctgc catgcacctg tccccctta atactgggca ttttaaagcc atctcaagag     2520
gcatcttcta catgttttgt acgcattaaa ataatttcaa agatatctga gaaaagccga    2580
tatttgccat tcttcctata tcctggaata tatcttgcat cctgagttta taataataaa    2640
taatattcta ccttggaaaa aaaaaaaaaa aaaaaaaaa aa                        2682
```

<210> SEQ ID NO 91
<211> LENGTH: 891
<212> TYPE: DNA
<213> ORGANISM: M. musculus

<400> SEQUENCE: 91

```
atgtctgcgg gagacccccg cgtgggatcc gggtccctgg actccttcat gttctccata     60
cccttggtcg cgcttaacgt gggagtgagg cgccgcctat cgctgttctt gaaccctcgg    120
acgcccgtgg cggccgactg gaccttgctg gcggaggaga tgggcttcga gtacttggag    180
atccgagagc tggaaacgcg ccctgacccc actcgcagtt tgttggatgc ctggcagggg    240
cgctctggcg cgtctgtcgg caggctgcta gagctgctgg ccttgttaga ccgtgaggat    300
atactgaagg agctgaagtc gcgcatcgag gaggactgcc agaaatactt aggtaagcag    360
cagaaccagg agtccgagaa gcctttacag gtggccagag tggaaagcag tgtcccacaa    420
acaaaggaac tgggaggcat caccacccct gatgacccc taggacaaac gccggaactt    480
ttcgatgcct ttatctgcta ctgccccaat gatatcgagt ttgtgcagga gatgatccgg    540
caactagaac agacagacta tcggcttaag ttgtgtgtgt ccgaccgtga cgtcctgccg    600
ggcacctgtg tctggtccat tgccagcgag ctaattgaga aaaggtgtcg ccgcatggtg    660
gtggttgttt ctgacgatta tctacagagc aaggaatgtg acttccagac caagtttgca    720
ctcagcctgt ctccaggtgt ccaacagaar cgactgattc ctattaaata caaggcgatg    780
aagaaggact ttcccagtat cctgcggttc atcactatat gcgattatac caaccccttgc    840 accaagtcct ggttctggac ccgccttgcc aaggctttgt ccctgccctg a             891
```

<210> SEQ ID NO 92
<211> LENGTH: 20
<212> TYPE: DNA
<213> ORGANISM: Artificial Sequence
<220> FEATURE:
<223> OTHER INFORMATION: PCR Primer

<400> SEQUENCE: 92

```
cagaggagga ttgccaaaag                                                 20
```

<210> SEQ ID NO 93
<211> LENGTH: 19
<212> TYPE: DNA
<213> ORGANISM: Artificial Sequence
<220> FEATURE:
<223> OTHER INFORMATION: PCR Primer

<400> SEQUENCE: 93

-continued ggggtcatca agtgtggtg                                                19

<210> SEQ ID NO 94
<211> LENGTH: 21
<212> TYPE: DNA
<213> ORGANISM: Artificial Sequence
<220> FEATURE:
<223> OTHER INFORMATION: PCR Probe

<400> SEQUENCE: 94
gcagtgtccc cacggacagc a                                             21

<210> SEQ ID NO 95
<211> LENGTH: 20
<212> TYPE: DNA
<213> ORGANISM: Artificial Sequence
<220> FEATURE:
<223> OTHER INFORMATION: PCR Primer

<400> SEQUENCE: 95
tgccctgaag actgttctga                                               20

<210> SEQ ID NO 96
<211> LENGTH: 20
<212> TYPE: DNA
<213> ORGANISM: Artificial Sequence
<220> FEATURE:
<223> OTHER INFORMATION: PCR Primer

<400> SEQUENCE: 96
actggttcca tgcaggacat                                               20

<210> SEQ ID NO 97
<211> LENGTH: 22
<212> TYPE: DNA
<213> ORGANISM: Artificial Sequence
<220> FEATURE:
<223> OTHER INFORMATION: PCR Probe

<400> SEQUENCE: 97
tgtctgcctg tccatgtact tc                                            22

<210> SEQ ID NO 98
<211> LENGTH: 19
<212> TYPE: DNA
<213> ORGANISM: Artificial Sequence
<220> FEATURE:
<223> OTHER INFORMATION: PCR Primer

<400> SEQUENCE: 98
cactcgagtt tgttggatg                                                19

<210> SEQ ID NO 99
<211> LENGTH: 20
<212> TYPE: DNA
<213> ORGANISM: Artificial Sequence
<220> FEATURE:
<223> OTHER INFORMATION: PCR Primer

<400> SEQUENCE: 99
ccacctgtaa aggcttctcg                                               20

<210> SEQ ID NO 100
<211> LENGTH: 22
<212> TYPE: DNA

```
<213> ORGANISM: Artificial Sequence
<220> FEATURE:
<223> OTHER INFORMATION: PCR Probe

<400> SEQUENCE: 100
gctcgtagag ctgctggcct tg                                              22

<210> SEQ ID NO 101
<211> LENGTH: 20
<212> TYPE: DNA
<213> ORGANISM: Artificial Sequence
<220> FEATURE:
<223> OTHER INFORMATION: PCR Primer

<400> SEQUENCE: 101
catggtggtg gttgtttctg                                                 20

<210> SEQ ID NO 102
<211> LENGTH: 20
<212> TYPE: DNA
<213> ORGANISM: Artificial Sequence
<220> FEATURE:
<223> OTHER INFORMATION: PCR Primer

<400> SEQUENCE: 102
cttggtgcaa gggttggtat                                                 20

<210> SEQ ID NO 103
<211> LENGTH: 22
<212> TYPE: DNA
<213> ORGANISM: Artificial Sequence
<220> FEATURE:
<223> OTHER INFORMATION: PCR Probe

<400> SEQUENCE: 103
tcagcctgtc tccaggtgtc ca                                              22

<210> SEQ ID NO 104
<211> LENGTH: 22
<212> TYPE: DNA
<213> ORGANISM: Artificial Sequence
<220> FEATURE:
<223> OTHER INFORMATION: PCR Primer

<400> SEQUENCE: 104
catagagacc ccgttgccta aa                                              22

<210> SEQ ID NO 105
<211> LENGTH: 22
<212> TYPE: DNA
<213> ORGANISM: Artificial Sequence
<220> FEATURE:
<223> OTHER INFORMATION: PCR Primer

<400> SEQUENCE: 105
tggctatctt cttgcacatt gc                                              22

<210> SEQ ID NO 106
<211> LENGTH: 23
<212> TYPE: DNA
<213> ORGANISM: Artificial Sequence
<220> FEATURE:
<223> OTHER INFORMATION: PCR Probe

<400> SEQUENCE: 106
ctcctgcctg ggaacaaccg gaa                                             23
```

```
<210> SEQ ID NO 107
<211> LENGTH: 25
<212> TYPE: DNA
<213> ORGANISM: Artificial Sequence
<220> FEATURE:
<223> OTHER INFORMATION: PCR Primer

<400> SEQUENCE: 107
gaaggaacca tctcactgtg tgtaa                                              25

<210> SEQ ID NO 108
<211> LENGTH: 21
<212> TYPE: DNA
<213> ORGANISM: Artificial Sequence
<220> FEATURE:
<223> OTHER INFORMATION: PCR Primer

<400> SEQUENCE: 108
aaatcaggaa ggctgccaag a                                                  21

<210> SEQ ID NO 109
<211> LENGTH: 23
<212> TYPE: DNA
<213> ORGANISM: Artificial Sequence
<220> FEATURE:
<223> OTHER INFORMATION: PCR Probe

<400> SEQUENCE: 109
catgacttcc aagctggccg tgg                                                23

<210> SEQ ID NO 110
<211> LENGTH: 21
<212> TYPE: DNA
<213> ORGANISM: Artificial Sequence
<220> FEATURE:
<223> OTHER INFORMATION: PCR Primer

<400> SEQUENCE: 110
tctcttcaag ggacaaggct g                                                  21

<210> SEQ ID NO 111
<211> LENGTH: 20
<212> TYPE: DNA
<213> ORGANISM: Artificial Sequence
<220> FEATURE:
<223> OTHER INFORMATION: PCR Primer

<400> SEQUENCE: 111
gatagcaaat cggctgacgg                                                    20

<210> SEQ ID NO 112
<211> LENGTH: 24
<212> TYPE: DNA
<213> ORGANISM: Artificial Sequence
<220> FEATURE:
<223> OTHER INFORMATION: PCR Probe

<400> SEQUENCE: 112
cccgactacg tgctcctcac ccac                                               24

<210> SEQ ID NO 113
<211> LENGTH: 20
<212> TYPE: DNA
<213> ORGANISM: Artificial Sequence
<220> FEATURE:
```

```
<223> OTHER INFORMATION: PCR Primer

<400> SEQUENCE: 113
gctgaccagg aagccaacag                                              20

<210> SEQ ID NO 114
<211> LENGTH: 20
<212> TYPE: DNA
<213> ORGANISM: Artificial Sequence
<220> FEATURE:
<223> OTHER INFORMATION: PCR Primer

<400> SEQUENCE: 114
caggcagtcc aggaggtctg                                              20

<210> SEQ ID NO 115
<211> LENGTH: 22
<212> TYPE: DNA
<213> ORGANISM: Artificial Sequence
<220> FEATURE:
<223> OTHER INFORMATION: PCR Probe

<400> SEQUENCE: 115
catggccgca gtggcaaaga cc                                           22

<210> SEQ ID NO 116
<211> LENGTH: 21
<212> TYPE: DNA
<213> ORGANISM: Artificial Sequence
<220> FEATURE:
<223> OTHER INFORMATION: PCR Primer

<400> SEQUENCE: 116
agcttggaag acgatcagca a                                            21

<210> SEQ ID NO 117
<211> LENGTH: 28
<212> TYPE: DNA
<213> ORGANISM: Artificial Sequence
<220> FEATURE:
<223> OTHER INFORMATION: PCR Primer

<400> SEQUENCE: 117
aaactgctga actattgtag gagagatg                                     28

<210> SEQ ID NO 118
<211> LENGTH: 25
<212> TYPE: DNA
<213> ORGANISM: Artificial Sequence
<220> FEATURE:
<223> OTHER INFORMATION: PCR Probe

<400> SEQUENCE: 118
agatgccgtg tttgatggct ccagc                                        25

<210> SEQ ID NO 119
<211> LENGTH: 23
<212> TYPE: DNA
<213> ORGANISM: Artificial Sequence
<220> FEATURE:
<223> OTHER INFORMATION: PCR Primer

<400> SEQUENCE: 119
ttgttcagca gtttggctat cag                                          23
```

```
<210> SEQ ID NO 120
<211> LENGTH: 24
<212> TYPE: DNA
<213> ORGANISM: Artificial Sequence
<220> FEATURE:
<223> OTHER INFORMATION: PCR Primer

<400> SEQUENCE: 120
aaacccggat agtattgctt gtct                                            24

<210> SEQ ID NO 121
<211> LENGTH: 29
<212> TYPE: DNA
<213> ORGANISM: Artificial Sequence
<220> FEATURE:
<223> OTHER INFORMATION: PCR Probe

<400> SEQUENCE: 121
cagatgatgg caagctcacg gattcttct                                       29

<210> SEQ ID NO 122
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 122
cggcaactgg agacacaag                                                  19

<210> SEQ ID NO 123
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 123
tctggaagtc acattccttg c                                               21

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
cactcgcagt ttgttggatg                                                 20

<210> SEQ ID NO 125
<211> LENGTH: 22
<212> TYPE: DNA
<213> ORGANISM: Artificial Sequence
<220> FEATURE:
<223> OTHER INFORMATION: Oligomeric Compound

<400> SEQUENCE: 125
accgataacg ttgccggtga cg                                              22

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound
```

```
<400> SEQUENCE: 126
ctgtggggaa gagacagagt                                              20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
ctcctctgtg gggaagagac                                              20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
caatcctcct ctgtggggaa                                              20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
tttggcaatc ctcctctgtg                                              20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130 atactttttgg caatcctcct                                             20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
ccagggggtc atcaagtgtg                                              20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
cttacccagg gggtcatcaa                                              20

<210> SEQ ID NO 133
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 133
ggacccttac ccaggggtc                                               20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
gtattggacc cttacccagg                                              20

<210> SEQ ID NO 135
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 135
gaacagtatt ggacccttac                                              20

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
ctgtggagaa gagaagggtg                                              20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
ctcctctgtg gagaagagaa                                              20

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
cagtcctcct ctgtggagaa                                              20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
```

```
tctggcagtc ctcctctgtg                                                    20
```

\<210\> SEQ ID NO 140
\<211\> LENGTH: 20
\<212\> TYPE: DNA
\<213\> ORGANISM: Artificial Sequence
\<220\> FEATURE:
\<223\> OTHER INFORMATION: Oligomeric Compound

\<400\> SEQUENCE: 140

```
gtatttctgg cagtcctcct                                                    20
```

\<210\> SEQ ID NO 141
\<211\> LENGTH: 20
\<212\> TYPE: DNA
\<213\> ORGANISM: Artificial Sequence
\<220\> FEATURE:
\<223\> OTHER INFORMATION: Oligomeric Compound

\<400\> SEQUENCE: 141

```
ctaggggtc atcaagggtg                                                     20
```

\<210\> SEQ ID NO 142
\<211\> LENGTH: 20
\<212\> TYPE: DNA
\<213\> ORGANISM: Artificial Sequence
\<220\> FEATURE:
\<223\> OTHER INFORMATION: Oligomeric Compound

\<400\> SEQUENCE: 142

```
cttacctagg gggtcatcaa                                                    20
```

\<210\> SEQ ID NO 143
\<211\> LENGTH: 20
\<212\> TYPE: DNA
\<213\> ORGANISM: Artificial Sequence
\<220\> FEATURE:
\<223\> OTHER INFORMATION: Oligomeric Compound

\<400\> SEQUENCE: 143

```
gggcccttac ctaggggtc                                                     20
```

\<210\> SEQ ID NO 144
\<211\> LENGTH: 20
\<212\> TYPE: DNA
\<213\> ORGANISM: Artificial Sequence
\<220\> FEATURE:
\<223\> OTHER INFORMATION: Oligomeric Compound

\<400\> SEQUENCE: 144

```
gtactgggcc cttacctagg                                                    20
```

\<210\> SEQ ID NO 145
\<211\> LENGTH: 20
\<212\> TYPE: DNA
\<213\> ORGANISM: Artificial Sequence
\<220\> FEATURE:
\<223\> OTHER INFORMATION: Oligomeric Compound

\<400\> SEQUENCE: 145

```
gcacagtact gggcccttac                                                    20
```

\<210\> SEQ ID NO 146
\<211\> LENGTH: 4358
\<212\> TYPE: DNA
\<213\> ORGANISM: H. Sapiens

```
<400> SEQUENCE: 146
aagaggaagc gctggcagac aatgcgaccc gaccgcgctg aggctccagg accgcccgcc      60
atggctgcag gaggtcccgg cgcggggtct gcggccccgg tctcctccac atcctccctt     120
cccctggctg ctctcaacat gcgagtgcgg cgccgcctgt ctctgttctt gaacgtgcgg     180
acacaggtgg cggccgactg gaccgcgctg gcggaggaga tggactttga gtacttggag     240
atccggcaac tggagacaca agcggacccc actggcaggc tgctggacgc ctggcaggga     300
cgccctggcg cctctgtagg ccgactgctc gagctgctta ccaagctggg ccgcgacgac     360
gtgctgctgg agctgggacc cagcattggt gaggacgtcc ccttcctggc ctcgtacctg     420
gggggtgagg aggctgactt ccgcgcgcct cagcatcctg tctcccatgg agagacccca     480
tttcctgcct cggggggcccg aagaagcctg cagagggaga accatgcggg tcccgttcct     540
tcttaataac cggtcgcggt tattaagaag gactggagaa aggtccggat aggcggagat     600
gggaaggaag cagcttaggc agaggctttc aggtagggcc aggagtcaga atcaggcttc     660
tgtgggggca tctgggctgt ttcaagtaga gcaacaggac aggtggggcg attgacagtg     720
gactgtctta gaaacctcaa gtcctgggga aatgcagccc ttctttctac tcactggcac     780
ttacataata tacatgcata ggcgttggat acagccgccc acagacaggc acaccttgct     840
gagttggaat cactgcacca taaccagtgg gtctcctgag cctttctggc atgcccagcc     900
ccttgctcac atctgccctg gatcccagaa gaagcagacc taccttggta ccattcttag     960
gatccctagg aagggacaga gatacaaacc tgactttgat ggccttccag aaagccagaa    1020
caccactgac atccctttgg gtcagttaga gccagtggga gctcaacttc tcagagccgt    1080
tgagcttcgc gtggcaccag tgaactgggg aagccctcta gaacaaccca gccagaggag    1140
gtgggacagc ggctggatcc tgactgtggg taaagaggta ggcactccca gggaggctgc    1200
tttactctgt ctcttcccca cagaggagga ttgccaaaag tatatcttga agcagcagca    1260
ggaggaggct gagaagcctt tacaggtggc cgctgtagac agcagtgtcc cacggacagc    1320
agagctggcg ggcatcacca cacttgatga cccccctgggt aagggtccaa tactgttccc    1380
atgggacagg tggaatagga cattgtggtg ttaagagcat gggtgtttga agcagatggg    1440
ctgtgagacc ttgggcaagt cacttaatct ttctgagcct cagtttcctc acctaagaaa    1500
tggagataat agtcctacct ctggattgct gtgagatgct catgaaataa tgtctgtctc    1560
gtggttaatc cagagcttag cccctgaggt actcatcttt cctctcctgg aaagggcact    1620
ttctctgagg agtatcatct tgggaagggt gcagggccca gggttgccta ggcaggggac    1680
tcttggctgg atccctccca agccttccca tggagctctg accaccaccc ttgtgctctg    1740
cacccagggc atatgcctga gcgtttcgat gccttcatct gctattgccc cagcgacatc    1800
cagtttgtgc aggagatgat ccggcaactg gaacagacaa actatcgact gaagttgtgt    1860
gtgtctgacc gcgatgtcct gcctggcacc tgtgtctggt ctattgctag tgagctcatc    1920
gaaaagaggt tggctagaag gccacggggt gggtgcgtgg atgcatgaag ccctgccctg    1980
gggtccagat actgggcatc tcctcctagc tgtgcactgt ccagcctggg cacagtgggc    2040
ccttcctgaa gctattccca ggggatatgc tgaactaagt tgccacagga cctgcagcct    2100
gcccactctc ccctaggtgc cgccggatgg tggtggttgt ctctgatgat tacctgcaga    2160
gcaaggaatg tgacttccag accaaatttg cactcagcct ctctccaggt aagctcaacc    2220
ctgctctggc aagagaatga gggaatgtgt aggtggggcc tctggattgt cagccttccc    2280
```

| | |
|---|---|
| tccccaagga ctgtggatgc agtaccaaag aactgctgaa gatctctgca cacctgagca | 2340 |
| tgtgtgcatg tgtgtgcctt tttgtgtgag tgaatgtgtg ccaggggtac ttagatgggg | 2400 |
| gatggctgtt gttaaccctg gggttgaaga ctgggcttgt cccaccatgg ggcaagggcc | 2460 |
| tgatgccagc atggcacccc ttggcttgca ggtgcccatc agaagcgact gatccccatc | 2520 |
| aagtacaagg caatgaagaa agagttcccc agcatcctga ggttcatcac tgtctgcgac | 2580 |
| tacaccaacc cctgcaccaa atcttggttc tggactcgcc ttgccaaggc cttgtccctg | 2640 |
| ccctgaagac tgttctgagg ccctgggtgt gtgtgtatct gtctgcctgt ccatgtactt | 2700 |
| ctgccctgcc tcctcctttc gttgtaggag gaatctgtgc tctacttacc tctcaattcc | 2760 |
| tggagatgcc aacttcacag acacgtctgc agcagctgga catcacattt catgtcctgc | 2820 |
| atggaaccag tggctgtgag tggcatgtcc acttgctgga ttatcagcca ggacactata | 2880 |
| gaacaggacc agctgagact aagaaggacc agcagagcca gctcagctct gagccattca | 2940 |
| cacatcttca ccctcagttt cctcacttga ggagtgggat ggggagaaca gagagtagct | 3000 |
| gtgtttgaat ccctgtagga aatggtgaag catagctctg ggtctcctgg gggagaccag | 3060 |
| gcttggctgc gggagagctg gctgttgctg gactacatgc tggccactgc tgtgaccacg | 3120 |
| acactgctgg ggcagcttct tccacagtga tgcctactga tgcttcagtg cctctgcaca | 3180 |
| ccgcccattc cacttcctcc ttccccacag ggcaggtggg gaagcagttt ggcccagccc | 3240 |
| aaggagaccc caccttgagc cttatttcct aatgggtcca cctctcatct gcatctttca | 3300 |
| cacctcccag cttctgccca accttcagca gtgacaagtc cccaagagac tcgcctgagc | 3360 |
| agcttgggct gcttttcatt tccacctgtc aggatgcctg tggtcatgct ctcagctcca | 3420 |
| cctggcatga aagggatcc tggcctctgg catattcatc aagtatgagt ctggggatg | 3480 |
| agtcactgta atgatgtgag cagggagcct tcctccctgg gccacctgca gagagctttc | 3540 |
| ccaccaactt tgtaccttga ttgccttaca aagttatttg tttacaaaca gcgaccatat | 3600 |
| aaaagcctcc tgccccaaag cttgtgggca catgggcaca tacagactca catacagaca | 3660 |
| cacacatata tgtacagaca tgtactctca cacacacagg caccagcata cacacgtttt | 3720 |
| tctaggtaca gctcccagga acagctaggt gggaaagtcc catcactgag ggagcctaac | 3780 |
| catgtccctg aacaaaaatt gggcactcat ctattccttt tctcttgtgt ccctactcat | 3840 |
| tgaaaccaaa ctctggaaag gacccaatgt accagtattt atacctctaa tgaagcacag | 3900 |
| agagaggaag agagctgctt aaactcacac aacaatgaac tgcagacaca gctgttctct | 3960 |
| ccctctctcc ttcccagagc aatttatact ttaccctcag gctgtcctct ggggagaagg | 4020 |
| tgccatggtc ttaggtgtct gtgccccagg acagaccta ggaccctaaa tccaatagaa | 4080 |
| aatgcatatc tttgctccac tttcagccag gctggagcaa ggtaccttt cttaggatct | 4140 |
| tgggagggaa tggatgcccc tctctgcatg atcttgttga ggcatttagc tgccatgcac | 4200 |
| ctgtcccct ttaatactgg gcattttaaa gccatctcaa gaggcatctt ctacatgttt | 4260 |
| tgtacgcatt aaaataattt caaagatatc tgagaaaagc cgatatttgc cattcttcct | 4320 |
| atatcctgga atatatcttg catcctgagt ttataata | 4358 |

<210> SEQ ID NO 147
<211> LENGTH: 4041
<212> TYPE: DNA
<213> ORGANISM: M. musculus

<400> SEQUENCE: 147

| | |
|---|---|
| ggctggcagg agacttaagg gaagtaggaa actccacagg cgagcgtact ggacggcacc | 60 |

-continued

```
ggggggcccag ggttgcctgc catgtctgcg ggagacccccc gcgtgggatc cgggtccctg    120
gactccttca tgttctccat acccttggtc gcgcttaacg tgggagtgag gcgccgccta    180
tcgctgttct tgaaccctcg gacgcccgtg gcggccgact ggaccttgct ggcggaggag    240
atgggcttcg agtacttgga gatccgagag ctggaaacgc gccctgaccc cactcgcagt    300
ttgttggatg cctggcaggg gcgctctggc gcgtctgtcg gcaggctgct agagctgctg    360
gccttgttag accgtgagga tatactgaag gagctgaagt cgcgcatcgg tgaggaaacg    420
tgcttcctgg ctttgtgcca aggatcaacg aggctagcct tggcatatta atcttgttca    480
ttttttttctg gggtgcgcta gggaggaaga gagtgacagt cgaattttct gtcagtatgc    540
aggtcagcgt agggattggg agaggggtca aaaaccctga ggaaagatgg aaagagccta    600
ggcaaagacc ttcagttgta ccaagagtca agatctgctt ttctcgcggt atctcagttg    660
tgtcaggatc aaccggacaa gtgaggaccc cttccatcac tcactggcac tcagcacaac    720
accccccgccc cgcccacagt gaggtacacc ttgctagatg ggggtcacca ttctcattga    780
gcactaactg ggtgcctgag cccttctgac attcaatcct ctgctccgat gctctgtgc    840
cctgctagat gcccagtttg gctccattct ctagagcctt agaaagggaa ggcaggagga    900
aggctcagag aagcaggctg actttggagt cctctcagat gctcattttg ggagagtcca    960
aaaggaagtg ttagtttgta gagccatcca tggtaccagt ggctggggaa ggctcggccc    1020
aagtaggccc ttttttaaatt ttttttttttaa catttattta ttattataca taagtacact    1080
gtagctgcct gcagacacac cagaaaaggg cgtcagatct cattatgggt ggttgtggga    1140
tttgaactca ggaccttcgg aagagcagtc agtgctctta ccggctgagc catctcgcca    1200
gccccaagta ggctctttaa actaattcag gattttgagt gtgtgtacag cagcaacctg    1260
gggcatgggg ggcggggggtg tcggggatgg ggtgggagga ggagcctcta caccccttctc    1320
ttctccacag aggaggactg ccagaaatac ttaggtaagc agcagaacca ggagtccgag    1380
aagcctttac aggtggccag agtggaaagc agtgtcccac aaacaaagga actgggaggc    1440
atcaccaccc ttgatgaccc cctaggtaag ggcccagtac tgtgcccta ggtagaatag    1500
gtgggccaca gcctcaaaca tgtgacctgc agagggcatg gataccggaa gcagatggat    1560
ggacctggga ccttgggcaa gctgctcatt ctgagccttg gtttcccat ctaagaaatg    1620
ggaataatgg cagtcctctc ccagagtggt tctgagactt taatggcatg cctccatcat    1680
agttaaccgg gatttcatct gggaggaagt tatctgttca ctggtagaga gggcatgtat    1740
atgacattgc tttgatatgg atacaggccc aggttcccctt gatggaagac tccaggttgg    1800
gctccttcca gccttctgca gaggctgatt gattcccttg tccctgtcc tcaggacaaa    1860
cgccggaact tttcgatgcc tttatctgct actgccccaa cgatatcgag tttgtgcagg    1920
agatgatccg gcaactagaa cagacagact atcggcttaa gttgtgtgtg tccgaccgtg    1980
acgtcctgcc gggcacctgt gtctggtcca ttgccagcga gctaattgag aaaaggttgg    2040
ttaaacatct aagagggtag gtgggtgaat gcatgaaacc cagaggtcca gatgcaagga    2100
ctgtcctgct agctgggctc tgtcccgcct gggtaatgta gtccttcctg accccatcct    2160
ctgaaggaag tcaccgcagt gccactctcc ctcaggtgtc gccgcatggt ggtggttgtt    2220
tctgacgatt atctacagag caaggaatgt gacttccaga ccaagtttgc actcagcctg    2280
tctccaggta agcttaggcc tgcttttggtc aaagagagag tagagatata gccttaggat    2340
gatagtccag gaatgcaaaa ccaaagcact acagatctct gaggacggac ctgtgtactt    2400
```

```
ccttatgtag tggatatgta tcatggatac ctggttggtg gagagctggt gttagcccgt    2460
gctttaggga ctgagcctgt cccaccctag ggccccacgt ggtcctaata ccacaccctt    2520
tggccttcag gtgtccaaca gaagcgactg attcctatta aatacaaggc gatgaagaag    2580
gactttccca gtatcctgcg gttcatcact atatgcgact ataccaaccc ttgcaccaag    2640
tcctggttct ggacccgcct tgccaaggct ttgtccctgc cctgaagatg accctgggag    2700
ccctaggtat gtcagtctgt ctgtgttctt ccgcttgcct cctttgacac tgtagtgggg    2760
agcttgtggt ccgtctatcc ctagacatct acagtagcca gatgtcatct ctcaagtcct    2820
tacggaacca gtgactgcaa gtgacattat gacttgccgg gttgccagcc aggacagtgt    2880
ttatcagggc tgcatgagtc taagcgaagg actagttgag ctacatctca gacatctttg    2940
gcctcagggt ctcctcctga gaaacaggat atggagatca ggcagggaaa tagtgaggca    3000
ctcttctggc tatcctagga gacccagtgt gggctgaagg ggagctgaag gagcacacac    3060
tggctgttaa ggagcaccac aggcttgcca ggacagctgc tttgacctgc caaccttaaa    3120
ctccctttct tcctcccaca gggcagaggg gaagatgaga ctgatgcgga gccagattct    3180
ctgatgccgt cctgtctaca tctttgactc ccctgggctc aacccgtgtt caatgatgac    3240
tggcctgagc aactaggact gcctttcctc ccagccaccc atgcctgtgc acgcacctca    3300
gtacacacat gcctcctcgc acacacaggc atctgcatat gtgtgtttcc tttgggacag    3360
ctcccaagga tagctgagtg gaagagttct atcatcaagg gggcctggcc atctccctgg    3420
acaaaagtgg ggtgcctttg ctacaggtag tggcacgggc ctatagtttc agcatttggg    3480
aggtagaggc aggagaatca ggagttcaag cttatccttg gcaacacacc tagtttaagg    3540
tcagcctggg ctacatgaga gcctacctcc cccatcccct accccagaa aagaaggaaa    3600 atctggggc actgtggatt tctcctctct tttctctacc tgttgaaagc aaagtctatg    3660
aaggccccaa acatgatagc atttgggccc ttagtaagct gaagataaaa aggagaagct    3720
gtttggcttc gccccacaaa gcagctgcac gctcagctgt tttctcccca gcagcgaggt    3780
ttgcatcttc ttattccttt cacgttctct accatagagg caatgtcatg gtccctctca    3840
gggtacaccc catggccctg agtccccaag aaagcgagtc tcccctcagt gtctggggga    3900
ggaatgaggc ctctgtgcac gggctcatgg ggcatttcac tgcttgatgt tgagcattct    3960
aaagcaacct gtgtcaagtg taaacctcct ccacctgtgt tagaggtttc atgggaatgt    4020
caataaacaa aagaatggct c                                             4041
```

MODIFICATION OF MYD88 SPLICING USING MODIFIED OLIGONUCLEOTIDES

CROSS REFERENCE TO RELATED APPLICATIONS

This application claims the benefit of priority to U.S. provisional patent application Ser. No. 60/648,823, filed Jan. 31, 2005, which is herein incorporated by reference in its entirety.

INCORPORATION OF THE SEQUENCE LISTING

A paper copy of the sequence listing and a computer-readable form of the sequence listing, on diskette, containing the file named CORE0057USSEQ.txt, which was created on Jan. 20, 2006, are herein incorporated by reference.

FIELD OF THE INVENTION

The present invention provides compositions and methods for modulating the expression of MyD88 by altering the splicing of MyD88. In particular, this invention relates to compounds, particularly oligonucleotides, specifically hybridizable with nucleic acids encoding MyD88 which effect splicing of the gene. Such compounds have been shown to modulate expression and splicing of MyD88 in vitro and in vivo.

BACKGROUND OF THE INVENTION

MyD88 is an adaptor protein involved in interleukin-1 receptor (IL-1R) and Toll-like receptor (TLR) induced activation of NF-κB (Burns et al. 1998, *J. Biol. Chem.* 273: 12203-12209; Wesche et al. 1997, *Immunity* 7:837-847; Medzhitov et al. 1998, *Mol. Cell.* 2:253-258). Both human and mouse MyD88 proteins are composed of a C-terminal Toll/IL-1R homology (TIR) domain and an N-terminal death domain (DD). These domains are separated by a small intermediate domain (ID). MyD88 links the TIR domain of IL-1R/ TLR with the DD of the Ser/Thr kinase, IRAK-1. MyD88 also recruits IRAK-4 via its ID. This enables IRAK-4 to phosphorylate IRAK-1. Phosphorylated IRAK-1 then interacts with TRAF6, which in turn, transmits a signal leading to activation of the IκB kinase complex and JNK (Cao et al. 1996, *Nature* 383:443-446). This eventually results in the activation of transcription factor NF-κB. As MyD88 is known to play a central role in regulating signaling through IL-1 and Toll-receptors, various strategies have been used to demonstrate that inhibition of MyD88 function results in an alleviation of inflammatory responses. For example, in vitro this has been clearly demonstrated using MyD88 deficient cells (Schnare et al. 2000, *Curr. Biol.* 10: 1139-1142; Yamamoto et al. 2002, *Nature.* 420:324-329). In animals, genetic ablation of MyD88 produces a diminution of responses to IL-1β and an overall reduction in models of inflammation (Kawai et al. 1999, *Immunity* 11:115-122; Bjorkbacka et al. 2004, *Nature Med.* 10:416-421; Adachi et al. 1998, *Immunity* 9:143-150). MyD88 deficient mice demonstrate reduced pathology associated with polymicrobial sepsis (Weighardt et al. 2002, *J Immunol.* 169:2823-2827) and defects in T-cell proliferation and induction of acute phase proteins in response to IL-1β (Adachi et al. 1998, *Immunity* 9:143-150).

A lipopolysaccharide (LPS)-induced splice variant of MyD88, MyD88$_S$, which has been reported to function as a dominant-negative regulator of IL-1β- and LPS-induced NF-κB activation, has recently been identified (Janssens et al. 2002, *Curr. Biol.* 12:467-471). The MyD88 gene contains 5 exons (Hardiman et al. 1997, *Genomics.* 45:332-339). MyD88$_S$ is produced as the result of complete excision of exon II from the mature mRNA by alternative splicing. This leads to an in-frame deletion of the complete ID (amino acids 110-154). Although MyD88$_S$ still binds IL-1R and IRAK-1, it is defective in its ability to recruit IRAK-4 and induce subsequent IRAK-1 phosphorylation and NF-κB activation (Burns et al. 2003, *J. Exp. Med.* 197:263-268). The ability of MyD88$_S$ to function as a dominant negative regulator of IL-1β and LPS signaling suggests that strategies to modify MyD88 RNA splicing, such that MyD88$_S$ is expressed preferentially to the larger MyD88 isoform (referred to herein as MyD88$_L$), would be therapeutically valuable in treating inflammatory diseases associated with excessive IL-1R signaling.

Although variations in alternative splicing are widely recognized as a mechanism to generate molecular diversity and clearly contribute to certain diseases (Maniatis and Tasic, 2002, *Nature.* 418:236-243; Johnson et al. 2003, *Science.* 302:2141-2144; Yeo et al. 2004, *Proc. Natl. Acad. Sci. U.S.A.* 101:15700-15705), the development of pharmacological agents capable of controlling mRNA splicing has remained challenging. An approach that has recently gained significant acceptance is the use of chemically modified antisense oligonucleotides. When appropriately designed and directed to hybridize to RNA sequences adjacent to splice junctions, these have been shown to effectively modulate pre-mRNA splicing (Sazani and Kole, 2003, *J. Clin. Invest.* 112:481-486; Taylor et al. 1999, *Nat. Biotech.* 17:1097-1100; Garcia-Blanco et al. 2004, *Nat. Biotech.* 22:535-546).

U.S. Pre-Grant Publication 2005-0181476 discusses the identification of MyD88$_S$ and methods of modulating alternative splicing of MyD88 through RNA inhibition and use of antisense oligonucleotides.

A method of controlling the behavior of a cell through modulation of the processing of an mRNA target by contacting the cell with an antisense compound acting via a non-cleavage event is disclosed in U.S. Pat. No. 6,210,892 and U.S. Pre-Grant Publication 2002-0049173.

Taylor et al. (1999, *Nat. Biotech.* 17:1097-1100) and Karras et al. (2000, *Mol. Pharm.* 58:380-387) describe modified oligonucleotides for modulation of pre-mRNA splicing of Bcl-x and interleukin-5 receptor alpha, respectively.

Kole et al. (WO 94/26887 and U.S. Pat. Nos. 5,627,274; 5,916,808; 5,976,879; and 5,665,593) disclose methods of combating aberrant splicing using modified antisense oligonucleotides which do not activate RNase H.

Antisense technology is an effective means for modulating expression of one or more specific gene products and is uniquely useful in a number of therapeutic, diagnostic, and research applications. Provided herein are modified antisense compounds for use in modulation of MyD88 splicing.

SUMMARY OF THE INVENTION

Provided herein are antisense compounds targeting MyD88 for modulation of MyD88 splicing. In one aspect of the invention, the antisense compounds are designed to increase the ratio of MyD88$_S$ to MyD88$_L$ mRNA or protein. In another aspect of the invention, the antisense compounds increase the ratio of MyD88$_L$ to MyD88$_S$ mRNA or protein.

In one embodiment, the antisense compounds are targeted to the exon II donor site of a nucleic acid molecule encoding human MyD88. The antisense compounds provided herein are resistant to RNase H degradation. In preferred embodiments the antisense compounds are 12 to 50, 12 to 30, or 15 to 30 nucleobases in length. In one embodiment, the antisense compounds comprise at least one modified nucleotide. In another embodiment, the antisense compounds comprise a modified nucleotide at each position. In yet another embodiment, the antisense compounds are uniformly modified at each position.

In some embodiments of the invention, the modification of the antisense compounds is a sugar modification. Sugar modifications included, but are not limited to, 2'-O-(2-methoxyethyl), 2'-fluoro, locked nucleic acid and ethylene bridged nucleic acid. In one preferred embodiment, the sugar modification is 2'-O-(2-methoxyethyl). In some embodiments, the antisense compounds further comprise phosphorothioate internucleoside linkages.

Antisense compounds contemplated include compounds comprising at least an 8-nucleobase portion of one of the illustrated compounds. Also contemplated are antisense compounds having at least 70%, at least 75%, at least 80%, at least 85%, at least 90% or at least 95% identity with one of the illustrated antisense compounds.

Also provided herein are methods of modulating splicing of human MyD88 in cells or tissues, comprising contacting said cells or tissues with the antisense compounds described herein. In one aspect, the modulation of splicing results in an increase in the ratio of $MyD88_S$ to $MyD88_L$ mRNA. In another aspect, the modulation of splicing results in an increase in the ratio of $MyD88_S$ to $MyD88_L$ protein. In some embodiments, the cells or tissues are liver cells or tissues.

Further provided are methods of inhibiting IL-1β signaling and inhibiting toll-like receptor signaling in cells or tissues, comprising contacting said cells or tissues with the antisense compounds provided herein.

DETAILED DESCRIPTION OF THE INVENTION

Antisense technology is an effective means for reducing the expression of one or more specific gene products and is uniquely useful in a number of therapeutic, diagnostic, and research applications. Provided herein are antisense compounds useful for modulating gene expression and associated pathways via antisense mechanisms of action based on target degradation or target occupancy.

The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes or gene products involved in disease.

Given the role of MyD88 in inflammatory signaling pathways, and thus a variety of inflammatory diseases, therapeutic tools for modulating expression of MyD88 are desirable. Furthermore, the finding that alternative splicing of MyD88, such as occurs following LPS stimulation, results in production of a short form ($MyD88_S$) that acts as a repressor of IL-1 (inflammatory) signaling, provides a rationale for identifying compounds capable of modulating MyD88 splicing. The ideal compound would shift MyD88 splicing such that the ratio of splice products favors $MyD88_S$ over $MyD88_L$. Provided herein are antisense compounds that drive splicing of MyD88 toward the short form. The antisense compounds, referred to herein as "splice switching oligonucleotides," target regions of MyD88 pre-mRNA near the exon II splice acceptor site and splice donor site. The antisense compounds provided herein are modified such that they are resistant to degradation by RNase H and are presumed to function by an occupancy-based mechanism.

As used herein, the terms "target nucleic acid" and "nucleic acid molecule encoding MyD88" have been used for convenience to encompass DNA encoding MyD88, RNA (including pre-mRNA and mRNA or portions thereof) transcribed from such DNA, and also cDNA derived from such RNA.

As used herein, "targeting" or "targeted to" refer to the process of designing an oligomeric compound such that the compound hybridizes with a selected nucleic acid molecule.

As used herein, "hybridization" means the pairing of complementary strands of oligomeric compounds. In the context of the present invention, an oligomeric compound is specifically hybridizable when there is a sufficient degree of complementarity to avoid non-specific binding of the oligomeric compound to non-target nucleic acid sequences.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing.

As used herein, compounds "targeted to the exon II donor site of a nucleic acid molecule encoding MyD88" refers to an antisense compound provided herein which hybridizes with at least a portion of a region of a nucleic acid molecule encoding MyD88, wherein the region consists of the exon II donor site and the 20 nucleotides upstream (5') of the donor site and the 20 nucleotides downstream (3') of the donor site of MyD88.

As used herein, compounds "targeted to the exon II acceptor site of a nucleic acid molecule encoding MyD88" refers to an antisense compound provided herein which hybridizes with at least a portion of a region of a nucleic acid molecule encoding MyD88, wherein the region consists of the exon II acceptor site and the 20 nucleotides upstream (5') of the acceptor site and the 20 nucleotides downstream (3') of the acceptor site of MyD88.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice products" or "splicing products" are the mature mRNA molecules generated from the process of splicing a pre-mRNA. Alternatively spliced pre-mRNAs have at least two different splice products. For example, a first splicing product may contain an additional exon, or portion of an exon, relative to a second splicing product. Splice products of a selected pre-mRNA can be identified by a variety of different techniques well known to those of skill in the art.

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and mRNA. In the context of the present invention, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated.

As used herein "splice donor site" refers to a splice site found at the 5' end of an intron, or alternatively, the 3' end of an exon. Splice donor site is used interchangeably with "5' splice site." As used herein "splice acceptor site" refers to a splice site found at the 3' end of an intron, or alternatively, the 5' end of an exon. Splice acceptor site is used interchangeably with "3' splice site."

As used herein, compounds "resistant to RNase H degradation" are antisense compounds having a least one chemical modification that increases resistance of the compound to RNase H cleavage. Such modifications include, but are not limited to, nucleotides with sugar modifications. As used herein, a nucleotide with a modified sugar includes, but is not limited to, any nucleotide wherein the 2'-deoxyribose sugar has been substituted with a chemically modified sugar moiety. In the context of the present invention, chemically modified sugar moieties include, but are not limited to, 2'-O-(2-methoxyethyl), 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido, locked nucleic acid (LNA) and ethylene bridged nucleic acid (ENA). Modified compounds resistant to RNase H cleavage are thoroughly described herein and are well know to those of skill in the art.

As used herein, "uniformly modified" refers to antisense compounds having the same chemical modification or modifications at each nucleotide.

In accordance with the present invention are compositions and methods for modulating the expression of MyD88 (also known as MYD88; myeloid differentiation factor; and myeloid differentiation primary response gene 88). Listed in Table 1 are GENBANK® accession numbers of sequences used to design oligomeric compounds targeted to MyD88. Oligomeric compounds of the invention include oligomeric compounds which hybridize with one or more target nucleic acid molecules shown in Table 1, as well as oligomeric compounds which hybridize to other nucleic acid molecules encoding MyD88. The oligomeric compounds may target any region, segment, or site of nucleic acid molecules which encode MyD88. Suitable target regions, segments, and sites include, but are not limited to, the 5'UTR, the start codon, the stop codon, the coding region, the 3'UTR, the 5' cap region, introns, exons, intron-exon junctions, exon-intron junctions, and exon-exon junctions.

TABLE 1

Gene Target Names and Sequences

| Target Name | Species | Genbank ® # | SEQ ID NO |
|---|---|---|---|
| MyD88 | Human | AB026898.1 (nt 86001-91000) | 3 |
| MyD88 | Human | AL526415.1 | 10 |
| MyD88 | Human | NM_002468.1 | 11 |
| MyD88 | Human | U70451.1 | 90 |
| MyD88 | Mouse | NM_010851.1 | 91 |
| MyD88 | Human | NT_037565.3 (nt 119121-123478) | 146 |
| MyD88 | Mouse | NT_039482.1 (nt 5061829-5065869) | 147 |

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds in accordance with this invention comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 12 to 50 nucleobases. One having ordinary skill in the art will appreciate that this embodies antisense compounds of 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention comprise 12 to 30 nucleobases. One having ordinary skill in the art will appreciate that this embodies antisense compounds of 12, 13, 14, 15, 16, 17, 18, 19, 20, 21, 22, 23, 24, 25, 26, 27, 28, 29 or 30 nucleobases.

In some embodiments, the antisense compounds of the invention comprise 15 to 30 nucleobases. One having ordinary skill in the art will appreciate that this embodies antisense compounds of 15, 16, 17, 18, 19, 20, 21, 22, 23, 24, 25, 26, 27, 28, 29 or 30 nucleobases.

In one embodiment, the antisense compounds of the invention comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds of the invention comprise 20 to 24 nucleobases. One having ordinary skill in the art will appreciate that this embodies antisense compounds of 20, 21, 22, 23, or 24 nucleobases.

In one embodiment, the antisense compounds of the invention comprise 16 to 20 nucleobases. One having ordinary skill in the art will appreciate that this embodies antisense compounds of 16, 17, 18, 19 or 20 nucleobases.

In one embodiment, the antisense compounds of the invention comprise 20 nucleobases.

In one embodiment, the antisense compounds of the invention comprise 19 nucleobases.

In one embodiment, the antisense compounds of the invention comprise 18 nucleobases.

In one embodiment, the antisense compounds of the invention comprise 17 nucleobases.

In one embodiment, the antisense compounds of the invention comprise 16 nucleobases.

In one embodiment, the antisense compounds of the invention comprise 15 nucleobases.

In one embodiment, the antisense compounds of the invention comprise 14 nucleobases.

In one embodiment, the antisense compounds of the invention comprise 13 nucleobases.

Antisense compounds 8-80 nucleobases in length, and any length within the range, comprising a stretch of at least eight (8) consecutive nucleobases selected from within the illustrative antisense compounds are considered to be suitable antisense compounds.

Compounds of the invention include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases.

One having skill in the art armed with the antisense compounds illustrated herein will be able, without undue experimentation, to identify further antisense compounds.

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least 70%, or at least 75%, or at least 80%, or at least 85%, or at least 90%, or at least 92%, or at least 95%, or at least 97%, or at least 98%, or at least 99% sequence complementarity to a target region within the target nucleic acid sequence to which they are targeted. For example, an oligomeric compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Oligomeric compounds, or a portion thereof, may have a defined percent identity to a SEQ ID NO, or a compound having a specific ISIS number. This identity may be over the entire length of the oligomeric compound, or in a portion of the oligomeric compound (e.g., nucleobases 1-20 of a 27-mer may be compared to a 20-mer to determine percent identity of the oligomeric compound to the SEQ ID NO) It is understood by those skilled in the art that an oligonucleotide need not have an identical sequence to those described herein to function similarly to the oligonucleotides described herein. Shortened (i.e., deleted, and therefore non-identical) versions of oligonucleotides taught herein, or non-identical (i.e., one base replaced with another) versions of the oligonucleotides taught herein fall within the scope of the invention. Percent identity is calculated according to the number of bases that are identical to the SEQ ID NO or compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase oligonucleotide comprising the full sequence of a 20 nucleobase SEQ ID NO would have a portion of 100% identity with the 20 nucleobase SEQ ID NO while further comprising an additional 10 nucleobase portion. In the context of the invention, the full length of the modified sequence may constitute a single portion.

The oligomeric compounds of the invention also include compounds in which a different base is present at one or more of the nucleotide positions in the compound. For example, if the first nucleotide is an adenosine, compounds may be produced which contain thymidine, guanosine or cytidine at this position. This may be done at any of the positions of the oligomeric compound. These compounds are then tested using the methods described herein to determine their ability to inhibit expression of MyD88 mRNA.

As used herein, "targeting" or "targeted to" refer to the process of designing an oligomeric compound such that the compound hybridizes with a selected nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding MyD88" encompass DNA encoding MyD88, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes MyD88.

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Target regions may include, for example, a particular exon or intron, or may include only selected nucleobases within an exon or intron which are identified as appropriate target regions. Within regions of target nucleic acids are segments. "Segments" are defined as smaller or sub-portions of regions within a target nucleic acid. "Sites," as used in the present invention, are defined as unique nucleobase positions within a target nucleic acid. As used herein, the "target site" of an oligomeric compound is the 5'-most nucleotide of the target nucleic acid to which the compound binds.

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5° CUG, and 5' AUA, 5'ACG and 5° CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. "Start codon" and "translation initiation codon" refer to the codon or codons that are used in vivo to initiate translation of an mRNA transcribed from a gene encoding a protein, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with oligomeric compounds of the invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Consequently, the types of variants described herein are also suitable target nucleic acids.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of oligomeric compounds useful of the present invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds can have one or more modified internucleoside linkages. Modified oligonucleotide backbones containing a phosphorus atom therein include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene(methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Oligomeric compounds may also contain one or more substituted sugar moieties. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O(($CH_2$)$_n$O)$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON(($CH_2$)$_n$CH$_3$)$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy(2'-O—CH$_2$CH$_2$OCH$_3$, also known as 2'-O-(2-methoxyethyl) or 2'-MOE) (Martin et al., *Helv. Chim. Acta*, 1995, 78, 486-504), i.e., an alkoxyalkoxy group. A further modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O-(CH$_2$)$_2$—O—(CH$_2$)$_2$—N(CH$_3$)$_2$, also described in examples hereinbelow.

Other modifications include 2'-methoxy(2'-O—CH$_3$), 2'-aminopropoxy(2'-OCH$_2$CH$_2$CH$_2$NH$_2$), 2'-allyl(2'-CH$_2$—CH=CH$_2$), 2'-O-allyl(2'-O—CH$_2$—CH=CH$_2$) and 2'-fluoro(2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

The terms used to describe the conformational geometry of homoduplex nucleic acids are "A Form" for RNA and "B Form" for DNA. In general, RNA:RNA duplexes are more stable and have higher melting temperatures (Tm's) than DNA:DNA duplexes (Sanger et al., *Principles of Nucleic Acid Structure*, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger et al., *Principles of Nucleic Acid Structure*, 1984, Springer-Verlag; New York, N.Y.). As used herein, B-form geometry is inclusive of both C2'-endo pucker and O4'-endo pucker.

The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., Biochemistry, 1995, 34, 4969-4982; Horton et al., *J. Mol. Biol.*, 1996, 264, 521-533). Consequently, compounds that favor an A-form geometry can enhance stacking interactions, thereby increasing the relative Tm and potentially enhancing a compound's antisense effect.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. Also provided herein are oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

Another group of oligomeric compounds includes oligonucleotide mimetics. The term "mimetic" as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N(CH$_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene ($—CH_2—$) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. LNAs are commercially available from ProLigo (Paris, France and Boulder, Colo., USA).

An isomer of LNA that has also been studied is alpha-L-LNA which has been shown to have superior stability against a 3'-exonuclease. The alpha-L-LNAs were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA:LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sci. U.S.A., 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in Chemical and Engineering News, 2003, 81, 9). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-alpha-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., Helv. Chim. Acta, 1997, 80, 2426-2439; Steffens et al., *J. Am. Chem. Soc.*, 1999, 121, 3249-3255; Renneberg et al., *J. Am. Chem. Soc.*, 2002, 124, 5993-6002; and Renneberg et al., *Nucleic acids res.*, 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). A "substitution" is the replacement of an unmodified or natural base with another unmodified or natural base. "Modified" nucleobases mean other synthetic and natural nucleobases such as 5-methylcytosine(5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds of the present invention can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., *Nucleosides and Nucleotides*, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model to its complementary target DNA or RNA with a $\Delta T_m$ of up to 18° C. relative to 5-methyl cytosine (dC5$^{me}$), which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Pre-Grant Publication 20030158403.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus(3'-cap) or can be present on both termini of a single strand, or one or more termini of both strands of a double-stranded compound. This cap structure is not to be confused with the inverted methylguanosine "5' cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single- or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNaseL which cleaves both cellular and viral RNA. Cleavage products of the RNA target can be routinely detected by gel electrophoresis and, if necessary, associated nucleic acid hybridization techniques known in the art.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxynucleotide gap flanked by five non-deoxynucleotide wings. This is referred to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-$N^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, (5'-O-(4,4'-Dimethoxytriphenylmethyl)-2'-O-(2-methoxyethyl)-$N^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-$N^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxy-ethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O-(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy(2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., *Nucleic Acids Research*, 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., *J. Med. Chem.*, 1993, 36, 831-841) and U.S. Pat. No. 5,670,633.

2'-O-Methoxyethyl-substituted nucleoside amidites can be prepared routinely as per the methods of Martin, P., *Helvetica Chimica Acta*, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P=S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, 5,719,262, 6,559,279 and 6,762,281.

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound.

The main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl(2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

(2'-O-Me)-(2'-deoxy)-(2'-O-Me) Chimeric Phosphorothioate Oligonucleotides

Chimeric oligonucleotides having 2'-O-alkyl phosphorothioate and 2'-deoxy phosphorothioate oligonucleotide segments can be routinely synthesized by one skilled in the art, using, for example, an Applied Biosystems automated DNA synthesizer Model 394. Oligonucleotides can be synthesized using an automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. In one nonlimiting example, the standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligonucleotide is then recovered by an appropriate method (precipitation, column chromatography, volume reduced in vacuo) and analyzed by methods routine in the art.

(2'-O-(2-Methoxyethyl))-(2'-deoxy)-(2'-O-(2-Methoxyethyl)) Chimeric Phosphorothioate Oligonucleotides (2'-O-(2-methoxyethyl))-(2'-deoxy)-(-2'-O-(2-methoxyethyl)) chimeric phosphorothioate oligonucleotides can be prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'deoxy Phosphorothioate)-(2'-O-(2-Methoxyethyl)Phosphodiester Chimeric Oligonucleotides (2'-O-(2-methoxyethyl phosphodiester)-(2'-deoxy phosphorothioate)-(2'-O-(methoxyethyl)phosphodiester) chimeric oligonucleotides can be prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides can be synthesized according to U.S. Pat. No. 5,623,065.

Methods of oligonucleotide purification and analysis are known to those skilled in the art. Analysis methods include capillary electrophoresis (CE) and electrospray-mass spectroscopy. Such synthesis and analysis methods can be performed in multi-well plates.

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of MyD88. Thus, in one embodiment modulation of expression can mean increase or decrease in target RNA or protein levels. In another embodiment modulation of expression can mean an increase or decrease of one or more RNA splice products, or a change in the ratio of two or more splice products.

Modulation of MyD88 expression can be assayed in a variety of ways known in the art. MyD88 mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by MyD88 can be quantitated in a variety of ways well known in the art, such as immunoprecipitation, Western blot analysis (immunoblotting), ELISA or fluorescence-activated cell sorting (FACS). Antibodies directed to a protein encoded by MyD88 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997. Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Once one or more target regions, segments or sites have been identified, oligomeric compounds are designed which are sufficiently complementary to the target, i.e., hybridize sufficiently well and with sufficient specificity, to give the desired effect. The oligomeric compounds of the present invention can be targeted to features of a target nucleobase sequence.

The locations on the target nucleic acid to which active oligomeric compounds hybridize are hereinbelow referred to as "validated target segments." As used herein the term "validated target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 8 to about 80, or about 13 to about 80, or about 12 to about 50, or about 12 to about 30, or about 15 to about 30, or about 20 to about 30, or about 20 to about 24, or about 16 to about 20 nucleobases). Similarly validated target segments are represented by DNA or RNA sequences that comprise at least the 8 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that a validated oligomeric target segment can be represented by DNA or RNA sequences that comprise at least 8 consecutive nucleobases from an internal portion of the sequence of a validated target segment, and can extend in either or both directions until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases.

In another embodiment, the validated target segments identified herein can be employed in a screen for additional compounds that modulate the expression of MyD88. "Modulators" are those compounds that modulate the expression of MyD88 and which comprise at least an 8-nucleobase portion which is complementary to a validated target segment. The screening method comprises the steps of contacting a validated target segment of a nucleic acid molecule encoding MyD88 with one or more candidate modulators, and selecting for one or more candidate modulators which perturb the expression of a nucleic acid molecule encoding MyD88. Once it is shown that the candidate modulator or modulators are capable of modulating the expression of a nucleic acid molecule encoding MyD88, the modulator can then be employed in further investigative studies of the function of MyD88, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

The oligomeric compounds of the present invention can be utilized for diagnostics, therapeutics, prophylaxis and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions of the present invention are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Compounds of the invention can be used to modulate the expression of MyD88 in an animal, such as a human. In one non-limiting embodiment, the methods comprise the step of administering to said animal an effective amount of an antisense compound that inhibits expression of MyD88. In one embodiment, the antisense compounds of the present invention effectively inhibit the levels or function of MyD88 RNA. Because reduction in MyD88 mRNA levels can lead to alteration in MyD88 protein products of expression as well, such resultant alterations can also be measured. Antisense compounds of the present invention that effectively inhibit the levels or function of MyD88 RNA or protein products of expression are considered active antisense compounds. In one embodiment, the antisense compounds of the invention inhibit the expression of MyD88 causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

In another non-limiting embodiment, the methods comprise the step of administering to said animal an effective amount of an antisense compound that modulates splicing of MyD88 pre-mRNA.

For example, the reduction of the expression of MyD88 mRNA products can be measured in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The cells contained within said fluids, tissues or organs being analyzed can contain a nucleic acid molecule encoding MyD88 protein and/or the MyD88-encoded protein itself. For example, fluids, tissues or organs procured from an animal can be evaluated for expression levels of the target mRNA or protein. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The compounds of the present invention can be utilized in pharmaceutical compositions by adding an effective amount of a compound to a suitable pharmaceutically acceptable diluent or carrier. In one aspect, the compounds of the present invention inhibit the expression of MyD88. The compounds of the invention can also be used in the manufacture of a medicament for the treatment of diseases and disorders related to MyD88 expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of MyD88 expression in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

The oligomeric compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl)phosphate) derivatives according to the methods disclosed in WO 93/24510 or WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

The oligomeric compounds of the invention may also be formulated with active or inert ingredients, or a combination of both, for delivery via parenteral and non-parenteral routes of administration. Compositions and methods of preparing formulations are well known to those skilled in the art.

While certain compounds, compositions and methods of the present invention have been described with specificity in accordance with certain embodiments, the following examples serve only to illustrate the compounds of the invention and are not intended to limit the same. Each of the references, GENBANK® accession numbers, and the like recited in the present application is incorporated herein by reference in its entirety.

Example 1

Cell Culture and Treatment with Oligomeric Compounds

The effect of oligomeric compounds on target nucleic acid expression was tested in A549, T24 or b.END cells. The human lung carcinoma cell line A549 was obtained from the American Type Culture Collection (Manassas, Va.). A549 cells are routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells are routinely passaged by trypsinization and dilution when they reached approximately 90% confluence. Cells are seeded into 96-well plates (Falcon-Primaria #3872) at a density of approximately 5000 cells/well for use in oligomeric compound transfection experiments.

The transitional cell bladder carcinoma cell line T24 was obtained from the American Type Culture Collection (ATCC) (Manassas, Va.). T24 cells are routinely cultured in complete McCoy's 5A basal media (Invitrogen Life Technologies, Carlsbad, Calif.) supplemented with 10% fetal bovine serum (Invitrogen Life Technologies, Carlsbad, Calif.), penicillin 100 units per mL, and streptomycin 100 µg/mL (Invitrogen Life Technologies, Carlsbad, Calif.). Cells are routinely passaged by trypsinization and dilution when they reach 90% confluence. Cells are seeded into 96-well plates (Falcon-Primaria #3872) at a density of 7000 cells/well for treatment with the compound of the invention.

The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #3872) at a density of approximately 3000 cells/well for use in oligomeric compound transfection experiments.

RAW264.7 cells were obtained from the American Type Tissue Culture Collection, Rockville, Md.) and 293FT cells were obtained from Invitrogen Corp. (Carlsbad, Calif.). The cells were cultivated in DMEM supplemented with 10% fetal bovine serum.

When cells reach appropriate confluency, they are treated with oligonucleotide using Lipofectin™ as described. When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/Ml per 100 Nm oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

The concentrations of antisense oligonucleotides used herein are from 25 nM to 300 nM when the antisense oligonucleotide is transfected using a liposome reagent and 1 µM to 40 µM when the antisense oligonucleotide is transfected by electroporation.

Example 2

Analysis of Oligonucleotide Inhibition of MyD88 Expression

Antisense modulation of MyD88 expression can be assayed in a variety of ways known in the art. For example, MyD88 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M et al., *Current Protocols in Molecular Biology*, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of MyD88 can be quantitated in a variety of ways well known in the art, such as immunoprecipitation, Western blot analysis (immunoblotting), ELISA or fluorescence-activated cell sorting (FACS). Antibodies directed to MyD88 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 3

Poly(A)+ mRNA Isolation

Poly(A)+ mRNA was isolated according to Miura et al., *Clin. Chem.*, 1996, 42, 1758-1764. Other methods for poly(A)+ mRNA isolation are taught in, for example, Ausubel, F. M. et al., *Current Protocols in Molecular Biology*, Volume 1, pp. 4.5.1-4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 4

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 5

Real-Time Quantitative PCR Analysis of MyD88 mRNA Levels

Quantitation of MyD88 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc. (Alameda, Calif.) or PE-Applied Biosystems (Foster City, Calif.)) is attached to the 5' end of the probe and a quencher dye (e.g., TAMRA, obtained from either Operon Technologies Inc. or PE-Applied Biosystems) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems. RT-PCR reactions were carried out by adding 25 µL PCR cocktail (1× TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368-374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human MyD88 were designed to hybridize to a human MyD88 sequence, using published sequence information (a truncated version containing bases 86001 to 91000 of GenBank accession number AB026898.1, incorporated herein as SEQ ID NO: 3). For human MyD88 the PCR primers were:

forward primer: GGGCTGCTTTTCATTTCCAC (SEQ ID NO: 4)

reverse primer: AGGCCAGGATCCCTTCTCAT (SEQ ID NO: 5) and the PCR probe was: FAM-AGGATGCCTGTG-GTCATGCTCTCAGC-TAMRA (SEQ ID NO: 6) where FAM (PE-Applied Biosystems) is the fluorescent reporter dye) and TAMRA (PE-Applied Biosystems) is the quencher dye. For human GAPDH the PCR primers were:

forward primer: GAAGGTGAAGGTCGGAGTC(SEQ ID NO: 7)

reverse primer: GAAGATGGTGATGGGATTTC (SEQ ID NO: 8) and the PCR probe was: 5' JOE-CAAGCTTCCCGT-TCTCAGCC-TAMRA 3' (SEQ ID NO: 9) where JOE (PE-Applied Biosystems) is the fluorescent reporter dye) and TAMRA (PE-Applied Biosystems) is the quencher dye.

Example 6

Northern Blot Analysis of MyD88 mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N. J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALNKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human MyD88, a human MyD88 specific probe was prepared by PCR using the forward primer GGGCT-GCTTTTCATTTCCAC (SEQ ID NO: 4) and the reverse primer AGGCCAGGATCCCTTCTCAT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 7

Antisense Inhibition of Human MyD88 Expression by Chimeric Phosphorothioate Oligonucleotides having 2'-MOE Wings and a Deoxy Gap In accordance with the present invention, a series of oligonucleotides were designed to target different regions of the human MyD88 RNA, using published sequences (residues 86001-91000 from GenBank accession number AB026898.1, incorporated herein as SEQ ID NO: 3, GenBank accession number AL526415.1, incorporated herein as SEQ ID NO: 10, and GenBank accession number NM_002468.1, incorporated herein as SEQ ID NO: 11). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human MyD88 mRNA levels by quantitative real-time PCR as described in other examples herein. Data are averages from two experiments. If present, "N.D." indicates "no data".

TABLE 2

Inhibition of human MyD88 mRNA levels by chimeric phosphorothioate oligonucleotides having 2'-MOE wings and a deoxy gap

| ISIS # | REGION | TARGET SEQ ID NO | TARGET SITE | SEQUENCE | % INHIBITION | SEQ ID NO |
|---|---|---|---|---|---|---|
| 190933 | 5'UTR | 3 | 9 | gtcgcattgtctgccagcgc | 0 | 12 |
| 190935 | 5'UTR | 3 | 14 | gtcgggtcgcattgtctgcc | 16 | 13 |
| 190937 | 5'UTR | 3 | 31 | cctggagcctcagcgcggtc | 59 | 14 |
| 190939 | 5'UTR | 3 | 36 | gcggtcctggagcctcagcg | 55 | 15 |
| 190941 | Start Codon | 3 | 45 | ccatggcgggcggtcctgga | 42 | 16 |
| 190943 | Start Codon | 3 | 53 | tcctgcagccatggcgggcg | 43 | 17 |
| 190945 | Start Codon | 3 | 60 | cgggacctcctgcagccatg | 81 | 18 |
| 190947 | Coding | 3 | 122 | catgttgagagcagccaggg | 27 | 19 |
| 190949 | Coding | 3 | 128 | cactcgcatgttgagagcag | 65 | 20 |
| 190951 | Coding | 3 | 156 | cgttcaagaacagagacagg | 10 | 21 |
| 190953 | Coding | 3 | 164 | tgtccgcacgttcaagaaca | 35 | 22 |
| 190955 | Coding | 3 | 214 | tactcaaagtccatctcctc | 0 | 23 |
| 190957 | Coding | 3 | 220 | tccaagtactcaaagtccat | 53 | 24 |
| 190959 | Coding | 3 | 230 | ttgccggatctccaagtact | 81 | 25 |

TABLE 2-continued

Inhibition of human MyD88 mRNA levels by chimeric phosphorothioate oligonucleotides having 2'-MOE wings and a deoxy gap

| ISIS # | REGION | TARGET SEQ ID NO | TARGET SITE | SEQUENCE | % INHIBITION | SEQ ID NO |
|---|---|---|---|---|---|---|
| 190961 | Coding | 3 | 238 | gtctccagttgccggatctc | 87 | 26 |
| 190963 | Coding | 3 | 269 | gtccagcagcctgccagtgg | 75 | 27 |
| 190965 | Coding | 3 | 308 | cagtcggcctacagaggcgc | 65 | 28 |
| 190967 | Coding | 3 | 317 | cagctcgagcagtcggccta | 54 | 29 |
| 190969 | Coding | 3 | 323 | ggtaagcagctcgagcagtc | 30 | 30 |
| 190971 | Coding | 3 | 332 | gcccagcttggtaagcagct | 84 | 31 |
| 190973 | Coding | 3 | 338 | gtcgcggcccagcttggtaa | 45 | 32 |
| 190975 | Coding | 3 | 371 | ctcaatgctgggtcccagct | 69 | 33 |
| 190977 | Coding | 3 | 382 | tggcaatcctcctcaatgct | 41 | 34 |
| 190979 | Coding | 3 | 401 | ctgcttcaagatatactttt | 76 | 35 |
| 190981 | Coding | 3 | 416 | agcctcctcctgctgctgct | 79 | 36 |
| 190983 | Coding | 3 | 425 | aggcttctcagcctcctcct | 84 | 37 |
| 190985 | Coding | 3 | 436 | gccacctgtaaaggcttctc | 80 | 38 |
| 190987 | Coding | 3 | 451 | ctgctgtctacagcggccac | 57 | 39 |
| 190989 | Coding | 3 | 466 | gctgtccgtgggacactgct | 84 | 40 |
| 190991 | Coding | 3 | 473 | cagctctgctgtccgtggga | 57 | 41 |
| 190993 | Coding | 3 | 494 | atcaagtgtggtgatgcccg | 56 | 42 |
| 190995 | Coding | 3 | 520 | cgctcaggcatatgcccag | 52 | 43 |
| 190997 | Coding | 3 | 544 | caatagcagatgaaggcatc | 66 | 44 |
| 190998 | Coding | 3 | 578 | gatcatctcctgcacaaact | 77 | 45 |
| 190999 | Coding | 3 | 583 | tgccggatcatctcctgcac | 23 | 46 |
| 191000 | Coding | 3 | 588 | ccagttgccggatcatctcc | 16 | 47 |
| 191001 | Coding | 3 | 604 | cgatagtttgtctgttccag | 71 | 48 |
| 191002 | Coding | 3 | 610 | ttcagtcgatagtttgtctg | 32 | 49 |
| 191003 | Coding | 3 | 627 | ggtcagacacacacaacttc | 52 | 50 |
| 191004 | Coding | 3 | 636 | ggacatcgcggtcagacaca | 45 | 51 |
| 191005 | Coding | 3 | 660 | tagaccagacacaggtgcca | 81 | 52 |
| 191006 | Coding | 3 | 670 | tcactagcaatagaccagac | 44 | 53 |
| 191007 | Coding | 3 | 678 | cgatgagctcactagcaata | 66 | 54 |
| 191008 | Coding | 3 | 688 | cacctcttttcgatgagctc | 62 | 55 |
| 191009 | Coding | 3 | 697 | atccggcggcacctcttttc | 58 | 56 |
| 191010 | Coding | 3 | 718 | tcatcagagacaaccaccac | 0 | 57 |
| 191011 | Coding | 3 | 724 | aggtaatcatcagagacaac | 48 | 58 |
| 191012 | Coding | 3 | 729 | tctgcaggtaatcatcagag | 83 | 59 |
| 191013 | Coding | 3 | 734 | cttgctctgcaggtaatcat | 84 | 60 |

TABLE 2-continued

Inhibition of human MyD88 mRNA levels by chimeric phosphorothioate oligonucleotides having 2'-MOE wings and a deoxy gap

| ISIS # | REGION | TARGET SEQ ID NO | TARGET SITE | SEQUENCE | % INHIBITION | SEQ ID NO |
|---|---|---|---|---|---|---|
| 191014 | Coding | 3 | 745 | aagtcacattccttgctctg | 75 | 61 |
| 191015 | Coding | 3 | 750 | tctggaagtcacattccttg | 91 | 62 |
| 191016 | Coding | 3 | 757 | aatttggtctggaagtcaca | 27 | 63 |
| 191017 | Coding | 3 | 762 | gtgcaaatttggtctggaag | 79 | 64 |
| 191018 | Coding | 3 | 771 | agaggctgagtgcaaatttg | 53 | 65 |
| 191019 | Coding | 3 | 778 | cctggagagaggctgagtgc | 75 | 66 |
| 191020 | Coding | 3 | 784 | tgggcacctggagagaggct | 80 | 67 |
| 191021 | Coding | 3 | 795 | gtcgcttctgatgggcacct | 79 | 68 |
| 191022 | Coding | 3 | 822 | tcattgccttgtacttgatg | 81 | 69 |
| 191023 | Coding | 3 | 856 | gtgatgaacctcaggatgct | 74 | 70 |
| 191024 | Coding | 3 | 868 | tagtcgcagacagtgatgaa | 37 | 71 |
| 191025 | Coding | 3 | 873 | tggtgtagtcgcagacagtg | 78 | 72 |
| 191026 | Coding | 3 | 900 | tccagaaccaagatttggtg | 88 | 73 |
| 191027 | Coding | 3 | 907 | aggcgagtccagaaccaaga | 69 | 74 |
| 191028 | Coding | 3 | 912 | tggcaaggcgagtccagaac | 84 | 75 |
| 191029 | Coding | 3 | 918 | aggccttggcaaggcgagtc | 64 | 76 |
| 191030 | Coding | 3 | 924 | gggacaaggccttggcaagg | 45 | 77 |
| 191031 | 5'UTR | 2 | 2 | gggtgcccacctctaccctt | 0 | 78 |
| 191032 | 5'UTR | 2 | 33 | tctggagccccgagcaaaag | 0 | 79 |
| 191033 | 5'UTR | 2 | 38 | tacaatctggagccccgagc | 0 | 80 |
| 191034 | 5'UTR | 2 | 47 | gccctgccctacaatctgga | 0 | 81 |
| 191035 | Exon 1: Intron 1 | 1 | 753 | acgtcctcaccaatgctggg | 51 | 82 |
| 191036 | Intron 1 | 1 | 952 | tccgcctatccggacctttc | 36 | 83 |
| 191037 | Intron 1 | 1 | 1037 | aaacagcccagatgccccca | 29 | 84 |
| 191038 | Intron 1 | 1 | 1058 | cctgtcctgttgctctactt | 52 | 85 |
| 191039 | Exon 3 | 1 | 2293 | tctagccaacctctttttcga | 35 | 86 |
| 191040 | Exon 4: Intron 4 | 1 | 2573 | ttgagcttacctggagagag | 20 | 87 |
| 191041 | Intron 4 | 1 | 2694 | gctcaggtgtgcagagatct | 64 | 88 |
| 191042 | Intron 4: Exon 5 | 1 | 2856 | tgatgggcacctgcaagcca | 47 | 89 |

As shown in Table 2, SEQ ID NOs 14, 15, 16, 17, 18, 20, 24, 25, 26, 27, 28, 29, 31, 32, 33, 35, 36, 37, 38, 39, 40, 41, 42, 43, 44, 45, 48, 50, 51, 52, 53, 54, 55, 56, 58, 59, 60, 61, 62, 64, 65, 66, 67, 68, 69, 70, 72, 73, 74, 75, 76, 77, 82, 85, 88 and 89 demonstrated at least 42% inhibition of human MyD88 expression in this assay and are therefore preferred. The target sites to which these preferred sequences are complementary are herein referred to as "active sites" and are therefore preferred sites for targeting by compounds of the present invention.

Example 8

Western Blot Analysis of MyD88 Protein Levels

Whole cell extracts were prepared by lysing cells in RIPA buffer (1×PBS, 1% NP40, 0.1% deoxyolate, 0.1% SDS) containing complete protease inhibitor mix (Boehringer Mannheim). Protein concentration of the cell extracts was measured by Bradford assay (BioRad # 500-0201). Equal amounts of protein (10-20 µg) were resolved on a NuPAGE Novex 10% Bis-Tris gel in MES running buffer (Invitrogen) and transferred to PVDF membranes (Invitrogen). The membranes were blocked for 1 hour in TBS containing 0.05% Tween-20 (TBST) and 5% milk powder. After overnight incubation at 4° C. with a 1:500 dilution of a rabbit polyclonal MyD88 antibody (Abcam, ab2064 or eBioscience, 14-6223), the membranes were washed in PBS containing 0.05% Tween-20 and incubated with a 1:5000 dilution of goat anti-rabbit horseradish peroxidase conjugated antibody in blocking buffer. Membranes were washed and developed using Enhanced Chemiluminescent (ECL) detection system (Amersham). Subsequently membranes were blocked for 2 hours at room temperature in TBST plus 5% milk powder. After incubation at room temperature with a 1:5000 dilution of a mouse monoclonal tubulin antibody (Sigma #T-5168), the membranes were washed in PBS containing 0.1% Tween-20 and incubated with a 1:5000 dilution of goat anti-mouse horseradish peroxidase conjugated antibody in blocking buffer and developed as detailed above. Blots were quantitated by laser scanning densitometry.

Example 9

Analysis of RNA for Studies of MyD88 Splicing Modulation

Total RNA was harvested at the indicated times following the initiation of transfection using an RNeasy mini prep kit (Qiagen, Valencia, Calif.) according to the manufacturers protocol. For Northern blots, RNA was separated on 1.2% agarose gels containing 1.1% formaldehyde, then transferred to HyBond membranes (Amersham). Blots were hybridized with $[^{32}P]$dCTP random prime labeled cDNA probes specific for MyD88 exon II (bases 360-494 of Genbank Accession No. U70451, incorporated herein as SEQ ID NO: 90) or MyD88 exon V (bases 1138-1377 of Genbank Accession No. U70451) for 2 hours in Rapid-hyb solution (Amersham). Blots were washed with 2×SSC containing 0.1% SDS at room temperature, followed by 0.1×SSC containing 0.1% SDS at 60° C. Polysomes were isolated from cells as detailed by Laroia et al. (1999, Science 284:499-502). PolyA RNA was purified using a Dynabeads mRNA DIRECT kit according to the manufacturers protocol (Dyna1 Biotech # 610-11).

Quantitative RT-PCR (qRT-PCR) was performed by methods well known to those of skill in the art (Winer et al. 1999, Anal. Biochem. 270:41-49). Briefly, 200 ng of total RNA was analyzed in a final volume of 50 µl containing 200 nM gene specific PCR primers, 0.2 mM of each dNTP, 75 nM fluorescently labeled oligonucleotide probe, 1× RT-PCR buffer, 5 mM $MgCl_2$, 2U Platinum Taq DNA Polymerase (Invitrogen), and 8U ribonuclease inhibitor. Reverse transcription was performed for 30 minutes at 48° C. followed by PCR, which included 40 thermal cycles of 30 s at 94° C. and 1 minute at 60° C., using an ABI Prism 7700 Sequence Detector (Foster City, Calif.). Probes and primers to human and mouse MyD88 were designed to hybridize to a human MyD88 sequence (Genbank Accession No. U70451, incorporated herein as SEQ ID NO: 90) or a mouse MyD88 sequence (Genbank Accession No. NM_010851, incorporated herein as SEQ ID NO: 91), using published sequence information. Primers and probes were also designed for hybridization with human ICAM-1 (Genbank Accession No. J03132), human IL-8 (Genbank Accession No. M28130), mouse TNF-α (Genbank Accession No. M13049) and mouse SAA-1 (Genbank Accession No. NM_009117). All quantitative RT-PCR data was normalized to expression of non-target gene human C-raf kinase (Genbank Accession No. X03484), or mouse C-raf kinase (Genbank Accession No. AB057663). The sequences and target genes of all primers and probes are shown in Table 3.

TABLE 3

Primers and probes for quantitative RT-PCR

| Target Name | Species | Sequence Description | Sequence (5' to 3') | SEQ ID NO |
|---|---|---|---|---|
| MyD88 exon II | Human | Forward primer | CAGAGGAGGATTGCCAAAAG | 92 |
| MyD88 exon II | Human | Reverse primer | GGGGTCATCAAGTGTGGTG | 93 |
| MyD88 exon II | Human | Probe | GCAGTGTCCCCACGGACAGCA | 94 |
| MyD88 exon V | Human | Forward primer | TGCCCTGAAGACTGTTCTGA | 95 |

TABLE 3-continued

Primers and probes for quantitative RT-PCR

| Target Name | Species | Sequence Description | Sequence (5' to 3') | SEQ ID NO |
|---|---|---|---|---|
| MyD88 exon V | Human | Reverse primer | ACTGGTTCCATGCAGGACAT | 96 |
| MyD88 exon V | Human | Probe | TGTCTGCCTGTCCATGTACTTC | 97 |
| MyD88 exon II | Mouse | Forward primer | CACTCGAGTTTGTTGGATG | 98 |
| MyD88 exon II | Mouse | Reverse primer | CCACCTGTAAAGGCTTCTCG | 99 |
| MyD88 exon II | Mouse | Probe | GCTCGTAGAGCTGCTGGCCTTG | 100 |
| MyD88 exon V | Mouse | Forward primer | GATGGTGGTGGTTGTTTCTG | 101 |
| MyD88 exon V | Mouse | Reverse primer | CTTGGTGCAAGGGTTGGTAT | 102 |
| MyD88 exon V | Mouse | Probe | TCAGCCTGTCTCCAGGTGTCCA | 103 |
| ICAM-1 | Human | Forward primer | CATAGAGACCCCGTTGCCTAAA | 104 |
| ICAM-1 | Human | Reverse primer | TGGCTATCTTCTTGCACATTGC | 105 |
| ICAM-1 | Human | Probe | CTCCTGCCTGGGAACAACCGGAA | 106 |
| IL-8 | Human | Forward primer | GAAGGAACCATCTCACTGTGTGTAA | 107 |
| IL-8 | Human | Reverse primer | AAATCAGGAAGGCTGCCAAGA | 108 |
| IL-8 | Human | Probe | CATGACTTCCAAGCTGGCCGTGG | 109 |
| TNF-α | Mouse | Forward primer | TCTCTTCAAGGGACAAGGCTG | 110 |
| TNF-α | Mouse | Reverse primer | GATAGCAAATCGGCTGACGG | 111 |
| TNF-α | Mouse | Probe | CCCGACTACGTGCTCCTCAGCCAC | 112 |
| SAA-1 | Mouse | Forward primer | GCTGACCAGGAAGCCAACAG | 113 |
| SAA-1 | Mouse | Reverse primer | CAGGCAGTCCAGGAGGTCTG | 114 |
| SAA-1 | Mouse | Probe | CATGGCCGCAGTGGCAAAGACC | 115 |
| C-raf | Human | Forward primer | AGCTTGGAAGACGATCAGCAA | 116 |
| C-raf | Human | Reverse primer | AAACTGCTGAACTATTGTAGGAGAGATG | 117 |
| C-raf | Human | Probe | AGATGCCGTGTTTGATGGCTCCAGC | 118 |
| C-raf | Mouse | Forward primer | TTGTTCAGCAGTTTGGCTATCAG | 119 |
| C-raf | Mouse | Reverse primer | AAACCCGGATAGTATTGCTTGTCT | 120 |
| C-raf | Mouse | Probe | CAGATGATGGCAAGCTCACGGATTCTTCT | 121 |

For standard RT-PCR reactions, 5 μg of total RNA was reverse transcribed in the presence of oligo dT using SuperScriptII reverse transcriptase according to the manufacturer's protocol (Invitrogen). Following a one hour incubation at 42° C., the cDNA was diluted by the addition of 80 μl of water. Three μl of the diluted cDNA was combined with 15 μl HotStarTaq mix (Qiagen) and 2.5 μl each of 10 μM forward and reverse PCR primer in a final volume of 30 μl. The PCR reaction was the cycled 30 seconds at 94° C., 30 seconds at 72° C. and 2 minutes at 60° C. with 35 repetitions. Primers used for standard RT-PCR reactions are shown in Table 4.

TABLE 4

Primers for standard RT-PCR

| Target Name | Species | Sequence Description | Sequence (5' to 3') | SEQ ID NO |
|---|---|---|---|---|
| MyD88 | Human | Forward primer | CGGCAACTGGAGACACAAG | 122 |
| MyD88 | Human | Reverse primer | TCTGGAAGTCACATTCCTTGC | 123 |
| MyD88 | Mouse | Forward primer | CACTCGCAGTTTGTTGGATG | 124 |
| MyD88 | Mouse | Reverse primer | TCTGGAAGTCACATTCCTTGC | 123 |

The expected PCR product for MyD88$_L$ is 525 bp. MyD88 exon II is 135 bp in length, therefore the expected length for the MyD88$_S$ PCR fragment is 390 bp. Products were visualized by electrophoresis on 2% agarose gels stained with ethidium bromide.

Example 10

NF-κB Luciferase Assays

293FT cells were seeded in 24-well tissue culture plates at 40,000 cells/well. The following day, cells were transfected with oligonucleotide in the presence of Lipofectin Reagent as described in previous examples herein. Following an overnight incubation, pNFκB-Luc (BD Biosciences) and pRL-CMV (Promega) plasmids and were introduced into the cells using SuperFect Reagent (Qiagen) according to the manufacturer's protocol. The following morning cells were stimulated with 30 ng/ml IL-1β or 15 ng/ml TNF-α for 4 hours then harvested in 120 μl of Passive Lysis Buffer (Promega). 30 μl of lysate was added to each well of a black 96 well plate, followed by *Photinus* and *Renilla* luciferase activity measured using a Dual Luciferase Reporter Assay System (Promega) according to the manufacturer's protocol. Luminescence was measured using a Packard TopCount. pNFκB-Luc activity was normalized to pRL-CMV activity.

Example 11

RAW264.7 Activation Assays

RAW264.7 cells were suspended at $10^7$ cells/mL in DMEM+10% FCS. 90 μl of the cell suspension was transferred to a 90 μl electroporation cuvette to which ASOs were added at indicated concentrations. Cells were pulsed at 90V for 6 mS using a BTX electroporator, then transferred to 1 ml media and incubated 48 hours. Cells were then stimulated for 6 hours with 10 μg/mL LPS or 5 μM CpG oligonucleotide ISIS 12449 (ACCGATAACGTTGCCGGTGACG; SEQ ID NO: 125) for 4 hours. NF-κB activity was determined by accessing TNF-α mRNA levels in treated cells by quantitative RT-PCR as described in previous examples herein. All values were normalized to expression of C-raf kinase, a non-target gene.

Example 12

Animal Studies

Twelve-week old male C57 BL/6 mice were purchased from Jackson Laboratory (Bar Harbor, Me.) and maintained in compliance with Isis Institutional Animal Care and Use Committee Guidelines in an Association for Assessment and Accreditation of Laboratory Animal Care International (AAALAC)-accredited facility. Mice were injected intraperitoneally with 10-50 mg/kg of oligonucleotide in 200 μL of saline solution, every 2-3 days for a total of 4 to 9 doses. Where indicated, mice were challenged with 0.1 μg of recombinant mouse IL-1β (R&D Systems, Minneapolis, Minn.) in 200 μL of saline by intravenous injection twenty-four hours after last dose of oligonucleotide. Liver and spleen were collected from mice under anesthesia at 2 hours after IL-1β challenge or 24 hour after the final oligonucleotide dose and samples prepared for RNA and western blot analyses.

Example 13

Design and Screening of Modified Oligomeric Compounds for Modulation of MyD88 Splicing MyD88 mRNA has been shown to undergo alternative splicing in response to such signals as LPS stimulation, resulting in production of the short form of MyD88 (MyD88$_S$). The short form, which results from skipping of exon II, acts as a dominant negative inhibitor of IL-1R signaling. Altering the ratio of MyD88 splice products to increase the level of MyD88$_S$ would function to decrease the cellular inflammatory response.

To modulate splicing of MyD88 pre-mRNA, a series of antisense compounds was designed to hybridize with either human MyD88 (Genbank Accession No. NT_037565.3; SEQ ID NO: 146) or mouse MyD88 (Genbank Accession No. NT_039482.1; SEQ ID NO: 147). Shown in Table 5 and Table 6 are antisense oligonucleotides (splice switching oligonucleotides) targeting either the exon II acceptor site or exon II donor site of MyD88. Exon II of human MyD88 encompasses nucleotides 1224-1358 of SEQ ID NO: 146 and exon II of mouse MyD88 encompasses nucleotides 1331-1465 of SEQ ID NO: 147. Each compound is 20 nucleobases in length and uniformly modified with 2'-O-(2-methoxyethyl) nucleotides at each position. The internucleoside (backbone) linkages are phosphorothioate throughout the oligonucleotide. All cytidine residues are 5-methylcytidines. Bold residues indicate those complementary to MyD88 intronic sequence. The start site for each oligonucleotide (5'-most nucleotide of the target sequence to which the oligonucleotide binds) is shown relative to the exon II splice junction.

TABLE 5

Human MyD88 splice switching oligonucleotides

| ISIS # | Splice Site Target | Start Site | Sequence (5' to 3') | SEQ ID NO |
|---|---|---|---|---|
| 337840 | Acceptor | -20 | CTGTGGGGAAGAGACAGAGT | 126 |
| 337843 | Acceptor | -15 | CTCCTCTGTGGGAAGAGAC | 127 |
| 337842 | Acceptor | -10 | CAATCCTCCTCTGTGGGAA | 128 |
| 337844 | Acceptor | -5 | TTTGGCAATCCTCCTCTGTG | 129 |
| 337841 | Acceptor | 0 | ATACTTTTGGCAATCCTCCT | 130 |
| 337845 | Donor | -20 | CCAGGGGGTCATCAAGTGTG | 131 |
| 337848 | Donor | -15 | CTTACCCAGGGGGTCATCAA | 132 |
| 337847 | Donor | -10 | GGACCCTTACCCAGGGGGTC | 133 |
| 337849 | Donor | -5 | GTATTGGACCCTTACCCAGG | 134 |
| 337846 | Donor | 0 | GAACAGTATTGGACCCTTAC | 135 |

TABLE 6

Mouse MyD88 splice switching oligonucleotides

| ISIS # | Splice Site Target | Start Site | Sequence (5' to 3') | SEQ ID NO |
|---|---|---|---|---|
| 337850 | Acceptor | -20 | CTGTGGAGAAGAGAAGGGTG | 136 |
| 337853 | Acceptor | -15 | CTCCTCTGTGGAGAAGAGAA | 137 |
| 337852 | Acceptor | -10 | CAGTCCTCCTCTGTGGAGAA | 138 |
| 337854 | Acceptor | -5 | TCTGGCAGTCCTCCTCTGTG | 139 |
| 337851 | Acceptor | 0 | GTATTTCTGGCAGTCCTCCT | 140 |
| 337856 | Donor | -20 | CTAGGGGGTCATCAAGGGTG | 141 |
| 337859 | Donor | -15 | CTTACCTAGGGGGTCATCAA | 142 |
| 337857 | Donor | -10 | GGGCCCTTACCTAGGGGGTC | 143 |
| 337858 | Donor | -5 | GTACTGGGCCCTTACCTAGG | 144 |
| 337855 | Donor | 0 | GCACAGTACTGGGCCCTTAC | 145 |

To determine whether the MyD88 splice switching oligonucleotides are capable of modulating splicing MyD88, A549 cells were treated with 0, 25, 50, 100 or 200 nM of the human MyD88 antisense oligonucleotides shown in Table 5. After an overnight incubation, cells were harvested and total RNA isolated and subjected to RT-PCR. The PCR primers employed were designed with complementarity to sequence flanking exon II such that a 525 bp fragment would be produced from the MyD88$_L$ message while the MyD88$_S$ mRNA, lacking exon II, would yield a PCR fragment 135 bp shorter. The results of the transfection experiments showed untreated A549 cells primarily expressed the long form of MyD88. Antisense oligonucleotides targeting the exon II acceptor site (ISIS 337840-337844) had only a slight effect on splice site selection, with the long form being predominant. However, treatment of cells with antisense oligonucleotides targeted to the exon II donor site (ISIS 337845-337849) resulted in a noticeable shift from the long to the short form of MyD88.

Antisense oligonucleotides were also evaluated in a number of other cell lines (e.g., T24, 293FT, T47D and MCF-7) with similar results, demonstrating that the effectiveness of splice switching antisense oligonucleotides is not cell line dependent.

To further characterize antisense oligonucleotide efficacy, 293FT cells were treated with the most active antisense oligonucleotides at concentrations ranging from 50 to 200 nM. Total RNA was analyzed for expression of MyD88 by RT-PCR. The most potent oligonucleotide, ISIS 337846, caused an approximately 50% shift to the short form of MyD88 at a dose of 100 nM and greater than 80% shift at 200 nM. The potency of ISIS 337846 was also confirmed by quantitative RT-PCR. For qRT-PCR two probes were used. The sequence of one probe was designed to be complementary to exon II sequence only. This qRT-PCR probe can therefore recognize only the long form of MyD88 since exon II is not present in MyD88$_S$. A second probe was designed with complementarity to exon V sequence. This probe can recognize both long and short form of MyD88. When MyD88 message was measured using the exon V probe the amount of MyD88 message measured was not significantly reduced by treatment with ISIS 337846. Conversely, when MyD88 message was measured using the exon II probe, a dose dependant reduction in mRNA levels was observed with an IC$_{50}$ of approximately 100 nM, in close agreement with the potency estimated by standard RT-PCR. Since the reduction in target mRNA was observed with the probe that recognizes only the long form of the message, but not the probe that recognizes both the short and long form, it can be concluded that overall MyD88 message is not being reduced by oligonucleotide treatment. Rather, the ratios of the long and short forms of the message are being altered.

In order to further characterize the MyD88 message, Northern blots were performed using polysome associated RNA or polyA+ RNA isolated from ISIS 337846 transfected or mock-transfected A549 cells as described in previous examples herein. The blots were probed with a radiolabeled exon II or exon V specific DNA fragment. Treatment with ISIS 337846 had no effect on RNA levels when the exon V probe was utilized. In contrast, the signal detected by the exon II probe, which can only detect the long form of Myd88, was significantly reduced by ISIS 337846 as compared to the untreated control. These data support the conclusion that ISIS 337846 alters splicing of the Myd88 message, reducing the abundance of the long form and increasing the abundance of the short form. Since these blots were prepared with polysomal or polyA+ RNA rather than total RNA, it can also be implied that the short isoform is exported from the nucleus and is polysome associated, and is therefore being actively translated.

To confirm that the short isoform of the protein is expressed in oligonucleotide treated cells, Western blot analysis was performed. MCF-7 cells were treated at a concentration of 100 nM with ISIS 337846 or ISIS 337840, an oligonucleotide that promotes very little alternative splicing of the target RNA. RNA was isolated for RT-PCR and cell extracts were prepared for analysis of MyD88 protein expression by Western blot 48 hours post-oligonucleotide treatment. Full-length MyD88 was found to migrate at 35 kD in accordance with the predicted size of the full-length protein. While the control ASO had no effect on MyD88 protein expression, a truncated version of the protein migrating at the expected size of the MyD8*$^S$ product (~25 kD) was observed in cells treated with ISIS 337846. The relative ratios of the short to the long form of the MyD88 protein are approximately equal to those observed for the RNA isoforms as determined by RT-PCR of RNA isolated from the same cells.

Taken together, these studies demonstrate that MyD88 splicing switching oligonucleotides are capable of altering the ratio of MyD88$_S$ and MyD88$_L$ mRNA and protein without an overall reduction in total MyD88 mRNA and protein. While not wishing to be bound by theory, splice switching oligonucleotides may function by blocking use of the splice site to which they are targeted. Thus, splice switching oligonucleotides targeting MyD88 exon II splice sites induce skipping of exon II.

Example 14

Effect of ISIS 337846 on IL-1β Signaling

The effect of ISIS 337846 treatment on the expression of IL-1β inducible genes was assessed. ICAM-1 is an adhesion molecule expressed at low levels in resting endothelial cells that is markedly up-regulated in response to IL-1β and other cytokines (Springer, 1990, *Nature*. 346:425-434). IL-8 is a member of the chemokine gene superfamily, members of which promote the pro-inflammatory phenotype of macrophages, vascular smooth muscle cells and endothelial cells (Koch et al. 1992, *Science*. 258:1798-1801). Up-regulation of IL-8 in response to IL-1β stimulation has also been documented (Medzhitov et al. 1997, *Nature*. 388:394-397). T24 cells were treated at a concentration of 200 nM with ISIS 337846, ISIS 337840 or a negative control oligonucleotide. Cells were then stimulated for 4 hours with IL-1β at 0.1 ng/mL 44 hours post-transfection. Total RNA was harvested and quantitative RT-PCR performed using primer/probe sets for either ICAM-1 or IL-8. Both ICAM-1 and IL-8 message were strongly up-regulated by IL-1β. Treatment of the cells with either the non-target control oligonucleotide or with ISIS 337840, which induces little MyD88$_S$ expression, did not effect IL-1β signaling. However, treatment of cells with ISIS 337846 reduced IL-1β if dependant up-regulation of both genes.

The ability of ISIS 337846 to inhibit activation of a NF-κB luciferase reporter plasmid, pNFκB-Luc, was also examined. 293FT cells were transfected with antisense oligonucleotide at a concentration of 200 nM. The following day, pNFκB-Luc was introduced into the cells. After an overnight incubation, the cells were stimulated with IL-1β or TNF-α for 4 hours. Cells were harvested and assayed for luciferase activity. The results were normalized to a co-transfected *Renilla* luciferase reporter. Stimulation of cells with both TNF-α and IL-1β resulted in a marked increase in luciferase activity. Treatment of cells with control or ISIS 337840 had little effect on either IL-1β or TNF-α signaling. TNF-α signaling was also not affected in cells treated with ISIS 337846 in agreement with previous reports that TNF-α mediated induction of NF-κB is independent of MyD88 (Burns et al. 1998, *J. Biol. Chem*. 273:12203-12209). However, luciferase expression was significantly reduced in IL-1β stimulated cells treated with ISIS 337846.

These results support the idea that modulating the MyD88 splice product ratio to increase levels of MyD88$_S$ significantly reduces IL-1β signaling. These results are in accordance with previous studies showing MyD88$_S$ acts as a dominant-negative regulator of IL-1β-induced NF-κB activation.

Example 15

Comparison of Splice Switching, RNase H-Dependent and siRNA Oligomeric Compounds for Modulation of MyD88 Splicing The splice switching antisense oligonucleotide, ISIS 337846, was compared with a published MyD88 siRNA (Oshiumi et al. 2003, *Nature Immunol*. 4:161-167) and a highly active RNAse H-dependent antisense oligonucleotide targeting MyD88, ISIS 191015 (SEQ ID NO: 62) to determine if one antisense mechanism was substantially more effective than others. T47D cells were treated with oligonucleotide at 200 nM in the presence of Lipofectin reagent as described in previous Examples herein. After 48 hours, cells were harvested and RNA was isolated. MyD88 mRNA levels were measured by qRT-PCR using the exon II and exon V specific probes as described above. With RNase H-dependent or siRNA antisense treatment, reduction of MyD88 message was observed with either the exon II or exon V probe. In contrast, treatment with the splice switching antisense oligonucleotide, ISIS 337846, resulted in reduction of MyD88 mRNA when the exon II probe was employed, but showed no significant reduction of MyD88 message when the exon V probe was utilized.

These results were confirmed by Northern blot analysis. Each type of antisense compound reduced signal detected via the exon II probe to the same extent. In contrast, the signal detected by the exon V probe was significantly reduced by the RNase H-dependent and siRNA antisense compounds, but not by the splicing switching antisense oligonucleotide ISIS 337846. This confirms that ISIS 337846 works not by cleavage and degradation of the target message as RNase H-dependent and siRNA antisense compounds do, but by forcing the use of a specific alternative splice site.

Western blots prepared with lysates from the same cells were also performed. Treatment with the RNase H-dependent or siRNA antisense compounds resulted in significant reduction in MyD88 protein as compared to the untreated control. The splice switching oligonucleotide also resulted in a reduction of full length MyD88 protein; however, in contrast to the siRNA and RNase H-dependent oligonucleotide treated cells, MyD88$_S$ protein was also observed following treatment with ISIS 337846.

The overall potencies of the siRNA, RNase H-dependent, and splice switching antisense compounds were next compared. T24 cells were treated with antisense oligonucleotides at 25, 50, 100 and 200 nM. The following day RNA was isolated and mRNA levels accessed by qRT-PCR using the MyD88 exon II specific probe. The results indicate that all antisense compounds exhibit similar potencies with IC$_{50}$s in the 50-100 nM range.

Splicing, RNase H-dependent and siRNA antisense compounds were also evaluated for their ability to inhibit IL-1β-dependant NF-κB activation. 293FT cells were treated as described above with splicing, RNase H-dependent, and siRNA oligomeric compounds at 50, 100 and 200 nM. The following day the reporter plasmid pNFκB-luc was introduced into the cells. Activation of luciferase by IL-1β and TNF-α was assayed after an overnight incubation. The antisense compounds exhibited similar abilities to reduce IL-1β signaling and diminish luciferase levels, approximately 50% at the 50 nM dose. As expected, there was no effect of the antisense compound treatments on TNF-α signaling even at the highest dose.

Example 16

Inhibition of Toll-Like Receptor Signaling in Mouse Cells using MyD88 Antisense Compounds To determine whether treatment of mouse cells with MyD88 splice switching oligonucleotide inhibits Toll-like receptor (TLR) signaling, RAW 264.7 cells were treated with the mouse compounds targeting exon II of MyD88, shown in Table 6 above. Cells were electroporated with antisense compound at a concentration of 10 μM and total RNA was isolated after 48 h. RNA was subjected to RT-PCR using primers flanking exon II, as described in previous Examples herein. The results demonstrated that treatment with ISIS 337856 led to a significant alteration in the ratio of MyD88 splice products with the short form predominating.

The effect of MyD88 antisense oligonucleotide administration on TLR9 signaling was next determined. TLR9 is involved in the recognition of specific unmethylated CpG-ODN sequences that distinguish bacterial DNA from mammalian DNA. The MyD88-dependent signaling pathway is common to many TLRs as MyD88 deficient mice are unable to produce inflammatory cytokines in response to most TLR ligands (Adachi et al. 1998, *Immunity.* 9:143-150; Medzhitov et al. 1997, *Nature.* 388:394-397). RAW 264.7 cells, which have been shown to express active TLR9 (An et al. 2002, *Immunol. Lett.* 81:165-169; Rhee et al. 2000, *J. Biol. Chem.* 275:34035-34040), were electroporated with 10 μM of ISIS 337856 (a splice switching oligonucleotide), ISIS 337853 (a non-active control oligonucleotide), or ISIS 191015 (an RNase H-dependent oligonucleotide), which is complementary to both mouse and human MyD88 mRNA. After 48 hours cells were treated with a previously identified CpG oligonucleotide TLR9 activator (Henry et al. 2000, *J. Pharm. Exp. Ther.* 292:468-479) at a concentration of 5 μM. After 4 h, RNA was harvested and analyzed for expression of TNF-α mRNA by qRT-PCR. TLR9 activation resulted in a 3- to 4-fold increase in TNF-α mRNA. In cells treated with either the splice switching or RNase H-dependent oligonucleotide, CpG signaling, as measured by TNF-α induction, was reduced by greater than 50 percent, while the control antisense oligonucleotide had no effect.

These results indicate that compounds which reduce expression of either total MyD88 or MyD88$_L$ specifically are capable of reducing TLR signaling.

Example 17

Inhibition of IL-1β Signaling in Mouse Liver Following Treatment with MyD88 Antisense Compounds The ability of modified antisense compounds to regulate MyD88 splicing in mice was next evaluated. Twelve-week old male C57 BL/6 mice were treated twice weekly for two weeks at doses of 10, 25, and 50 mg/kg. 24 hours after the final antisense oligonucleotide treatment, liver RNA was isolated and subjected to RT-PCR using primers bracketing exon II of MyD88. At the 25 mg/kg dose there was an approximately equal distribution of MyD88$_L$ and MyD88$_S$. At 50 mg/kg the majority of the MyD88 RNA present is the short form. At both doses there is a general reduction in the total overall amount of MyD88 message. This observation was confirmed using quantitative RT-PCR. Liver RNA from the same experiment was analyzed by TaqMan RT-PCR using a primer/probe set specific to exon V of mouse MyD88. A corresponding loss in the MyD88 message was observed as the ASO dose was increased. Since this primer/probe set recognizes both MyD88 isoforms, the reduction cannot be attributed solely to oligonucleotide directed switching of splicing to the short form.

Lysates prepared from the livers of treated animals were also analyzed by Western blot. In agreement with the reduction observed at the RNA level, MyD88 protein levels were reduced at all treatment doses as compared to the saline treated control mice. Therefore, in vivo, the splicing ASO results in an overall reduction in MyD88 RNA and protein not observed in vitro. However, in contrast to cell culture experiments, no short form of the MyD88 protein was observed in vivo.

Activity of the splicing ASO was evaluated in other tissues. Treatment of mice with ISIS 337856 at a dose of 50 mg/Kg twice weekly for four weeks resulted in an approximately 60% reduction in MyD88 message in liver as assessed by quantitative RT-PCR using the exon V primer/probe set 24 hours after the final treatment. In intestine, the splice switching oligonucleotide reduced MyD88 message levels to 70% of the saline treated control. In adipose tissue, the splice switching oligonucleotide appeared to be even more active, reducing mRNA levels by almost 90%. Western blots performed using lysates from the same tissues showed that MyD88 protein was reduced in intestine and adipose tissue as well as liver in the ISIS 337856 treated animals, however, as in the liver, no short form of the protein was observed in the Western blots from either tissue.

To determine if antisense oligonucleotide mediated modulation of MyD88 splicing could disrupt IL-1β signaling in vivo, mice were dosed with 50 mg/kg of ISIS 337856 or a control oligonucleotide, 3 times weekly for three weeks. 24 hours after the final dose animals were challenged with 0.1 μg of IL-1β. After 2 hours, livers were taken and expression of MyD88 and serum amyloid A (SAA-1) RNA analyzed. Although a shift to MyD88$_S$ RNA was observed, overall expression of both isoforms of MyD88 was again found to be reduced by ISIS 337856 as determined by RT-PCR using primers flanking exon II. Liver SAA-1 levels were analyzed by quantitative RT-PCR. In agreement with a previous study demonstrating up-regulation of the SAA-1 gene in the liver of IL-1β treated mice (Adachi et al. 1998, *Immunity.* 9:143-150), SAA-1 mRNA was strongly up-regulated by IL-1β administration in saline treated mice. However, the IL-1β-mediated increase in SAA-1 expression was completely blocked mice treated with ISIS 337856. In contrast, the control oligonucleotide did not significantly effect IL-1β induction of SAA-1 mRNA expression.

These results demonstrate that splice switching oligonucleotides are active in vivo. Although overall MyD88 mRNA and protein expression was reduced, an increase in the ratio of MyD88$_S$ to MyD88$_L$ also was demonstrated by treatment with splice switching oligonucleotides in vivo.

What is claimed is:

1. A compound comprising a modified oligonucleotide consisting of 12 to 50 linked nucleosides and having a nucleobase sequence at least 80% complementary to the exon II donor site of a nucleic acid molecule encoding human MyD88 set forth in nucleotides 1338 to 1378 of SEQ ID NO: 146 as measured over the entirety of said modified oligonucleotide, and wherein each nucleoside of the modified oligonucleotide comprises a sugar modification.

2. The compound of claim 1 wherein the modified oligonucleotide consists of 12 to 30 linked nucleosides.

3. The compound of claim 1 wherein the modified oligonucleotide consists of 15 to 30 linked nucleosides.

4. The compound of claim 1, wherein, each nucleoside of the modified oligonucleotide comprises the same sugar modification.

5. The compound of claim 4 wherein the sugar modification is selected from the group consisting of 2'-O-methoxyethyl, 2'-fluoro, locked nucleic acid and ethylene bridged nucleic acid.

6. The compound of claim 5 wherein the sugar modification is 2'-O-methoxyethyl.

7. The compound of claim 6, wherein each internucleoside linkage of said modified oligonucleotide is a phosphorothioate internucleoside linkage.

8. The compound of claim 7, wherein said compound is single-stranded and not hybridized to a second strand in a duplex.

9. The compound of claim 1, wherein said compound is single-stranded and not hybridized to a second strand in a duplex.

10. A compound comprising a modified oligonucleotide consisting of 12 to 50 linked nucleosides and having a nucleobase sequence at least 80% complementary to the exon II donor site of a nucleic acid molecule encoding human MyD88 as set forth in SEQ ID NO: 146 as measured over the entirety of said modified oligonucleotide, wherein each nucleoside of the modified oligonucleotide comprises a sugar modification, and wherein the nucleobase sequence of the modified oligonucleotide has 100% identity to SEQ ID NO: 135 over the length of the modified oligonucleotide.

11. The compound of claim 10, wherein said compound is single-stranded and not hybridized to a second strand in a duplex.

12. A compound comprising a modified oligonucleotide consisting of 15 to 30 linked nucleosides and having a nucleobase sequence at least 80% complementary to the exon II donor site of a nucleic acid molecule encoding human MyD88 as set forth in SEQ ID NO: 146 as measured over the entirety of said modified oligonucleotide, wherein each nucleoside of the modified oligonucleotide comprises a sugar modification, and wherein the nucleobase sequence of the modified oligonucleotide has at least 80% identity to SEQ ID NO: 135 over the length of the modified oligonucleotide.

13. The compound of claim 12, wherein said compound is single-stranded and not hybridized to a second strand in a duplex.

14. The compound of claim 12, wherein the nucleobase sequence of the modified oligonucleotide has at least 90% identity to SEQ ID NO: 135 over the length of the modified oligonucleotide.

15. The compound of claim 12, wherein the nucleobase sequence of the modified oligonucleotide has at least 95% identity to SEQ ID NO: 135 over the length of the modified oligonucleotide.

16. A compound comprising a modified oligonucleotide consisting of 12 to 50 linked nucleosides and having a nucleobase sequence at least 90% complementary to the exon II donor site of a nucleic acid molecule encoding human MyD88 set forth in nucleotides 1338 to 1378 of SEQ ID NO: 146 as measured over the entirety of said modified oligonucleotide, wherein said nucleobase sequence comprises at least 8 consecutive nucleobases from the nucleobase sequence of SEQ ID NO:135, and wherein each nucleoside of the modified oligonucleotide comprises a sugar modification.

17. The compound of claim 16, wherein said nucleobase sequence is at least 95% complementary to the exon II donor site of a nucleic acid molecule encoding human MyD88 set forth in nucleotides 1338 to 1378 of SEQ ID NO: 146 as measured over the entirety of said modified oligonucleotide.

18. The compound of claim 16, wherein said compound is single-stranded and not hybridized to a second strand in a duplex.

19. The compound of claim 16, wherein the modified oligonucleotide consists of 12 to 30 linked nucleosides.

20. The compound of claim 16 wherein the modified oligonucleotide consists of 15 to 30 linked nucleosides.

21. The compound of claim 16, wherein each nucleoside of the modified oligonucleotide comprises the same sugar modification.

22. The compound of claim 21, wherein the sugar modification is selected from the group consisting of 2'-O-methoxyethyl, 2'-fluoro, locked nucleic acid and ethylene bridged nucleic acid.

23. The compound of claim 22, wherein the sugar modification is 2'-O-methoxyethyl.

24. The compound of claim 23, wherein each internucleoside linkage of said modified oligonucleotide is a phosphorothioate internucleoside linkage.

25. The compound of claim 24, wherein said compound is single-stranded and not hybridized to a second strand in a duplex.

26. A compound comprising a modified oligonucleotide consisting of 12 to 50 linked nucleosides and having a nucleobase sequence that is 100% complementary to the exon II donor site of a nucleic acid molecule encoding human MyD88 as set forth in nucleotides 1338 to 1378 of SEQ ID NO: 146 as measured over the entirety of said modified oligonucleotide, wherein said nucleobase sequence comprises at least 8 consecutive nucleobases from the nucleobase sequence of SEQ ID NO: 135, and wherein each nucleoside of the modified oligonucleotide comprises a sugar modification.

27. The compound of claim 26, wherein said compound is single-stranded and not hybridized to a second strand in a duplex.

* * * * *